US012589080B2

(12) United States Patent
Goldberg et al.

(10) Patent No.: US 12,589,080 B2
(45) Date of Patent: Mar. 31, 2026

(54) ENHANCED TWO-STAGE MICROPARTICLE-BASED LOCALIZED THERAPEUTIC DELIVERY SYSTEM

(71) Applicant: Privo Technologies, Inc., Peabody, MA (US)

(72) Inventors: Manijeh N. Goldberg, Newburyport, MA (US); Aaron M. Manzi, Haverhill, MA (US); Eric R. Goldberg, Newburyport, MA (US)

(73) Assignee: Privo Technologies, Inc., Peabody, MA (US)

( * ) Notice: Subject to any disclaimer, the term of this patent is extended or adjusted under 35 U.S.C. 154(b) by 0 days.

(21) Appl. No.: 17/830,078

(22) Filed: Jun. 1, 2022

(65) Prior Publication Data

US 2022/0387340 A1 Dec. 8, 2022

Related U.S. Application Data

(60) Provisional application No. 63/195,469, filed on Jun. 1, 2021.

(51) Int. Cl.
*A61K 9/51* (2006.01)
*A61K 9/00* (2006.01)
(Continued)

(52) U.S. Cl.
CPC ............ *A61K 9/5161* (2013.01); *A61K 9/006* (2013.01); *A61K 9/1611* (2013.01); *A61K 9/1652* (2013.01); *A61K 9/1682* (2013.01); *A61K 9/5115* (2013.01); *A61K 9/5123* (2013.01); *A61K 9/5146* (2013.01); *A61K 33/243* (2019.01); *A61K 47/10* (2013.01);
(Continued)

(58) Field of Classification Search
CPC ............................ A61K 9/5161; A61K 33/243
See application file for complete search history.

(56) References Cited

U.S. PATENT DOCUMENTS 3,983,173 A 9/1976 Hartung et al.
4,638,043 A 1/1987 Szycher et al.
(Continued)

FOREIGN PATENT DOCUMENTS

AU 2014218717 B2 1/2017
DE 10213427 A1 10/2003
(Continued)

OTHER PUBLICATIONS

Jonassen, H. et al., Stability of chitosan nanoparticles cross-linked with tripolyphosphate, Oct. 9, 2012, Biomacromolecules, vol. 13, 3747-3756 (Year: 2012).*
(Continued)

*Primary Examiner* — Dominic Lazaro
(74) *Attorney, Agent, or Firm* — Mintz, Levin, Cohn, Ferris, Glovsky and Popeo, P.C.

(57) ABSTRACT

A system is disclosed for delivery of a therapeutic agent to a site in mucosal tissue or to the skin of a patient. The system includes a porous mucoadhesive, freeze-dried matrix formed by a composition including chitosan in an aqueous salt solution of a chloride salt of a monovalent cation. The system further includes a plurality of chitosan microparticles having an average diameter between 500 nm and 2000 nm and comprising a therapeutic agent.

28 Claims, 7 Drawing Sheets

(51) Int. Cl.

| | |
|---|---|
| ***A61K 9/16*** | (2006.01) |
| ***A61K 33/243*** | (2019.01) |
| ***A61K 47/10*** | (2017.01) |
| ***A61K 47/26*** | (2006.01) |
| ***A61K 47/38*** | (2006.01) |
| ***A61P 17/06*** | (2006.01) |
| ***A61P 35/00*** | (2006.01) |
| *B82Y 5/00* | (2011.01) |

(52) U.S. Cl.
CPC .............. *A61K 47/26* (2013.01); *A61K 47/38* (2013.01); *A61P 17/06* (2018.01); *A61P 35/00* (2018.01); *B82Y 5/00* (2013.01)

(56) References Cited

U.S. PATENT DOCUMENTS

| | | | |
|---|---|---|---|
| 4,765,983 | A | 8/1988 | Takayanagi et al. |
| 4,895,724 | A | 1/1990 | Cardinal et al. |
| 4,997,425 | A | 3/1991 | Shioya et al. |
| 5,447,940 | A | 9/1995 | Harvey et al. |
| 5,855,904 | A | 1/1999 | Chung |
| 6,071,528 | A | 6/2000 | Jensen |
| 10,159,651 | B2 | 12/2018 | Goldberg et al. |
| 10,398,655 | B2 | 9/2019 | Goldberg et al. |
| 10,478,403 | B1 | 11/2019 | Goldberg et al. |
| 2003/0017195 | A1 | 1/2003 | Mitragotri et al. |
| 2003/0049208 | A1 | 3/2003 | Ream et al. |
| 2004/0106344 | A1 | 6/2004 | Looney et al. |
| 2004/0151774 | A1 | 8/2004 | Pauletti et al. |
| 2005/0013866 | A1 | 1/2005 | Maincent et al. |
| 2005/0137512 | A1 | 6/2005 | Campbell et al. |
| 2005/0147656 | A1 | 7/2005 | Mccarthy et al. |
| 2006/0210604 | A1 | 9/2006 | Dadey |
| 2007/0254016 | A1 | 11/2007 | Andersen et al. |
| 2008/0044478 | A1 | 2/2008 | Ramstack et al. |
| 2008/0220030 | A1 | 9/2008 | Alonso et al. |
| 2009/0018479 | A1 | 1/2009 | Mccarthy et al. |
| 2009/0280182 | A1 | 11/2009 | Beck et al. |
| 2009/0299328 | A1 | 12/2009 | Mudd et al. |
| 2010/0003300 | A1 | 1/2010 | Markland et al. |
| 2010/0112050 | A1 | 5/2010 | Ryoo et al. |
| 2010/0135979 | A1 | 6/2010 | Jederstrom et al. |
| 2010/0167401 | A1 | 7/2010 | Hasirci et al. |
| 2011/0044911 | A1 | 2/2011 | Engel et al. |
| 2011/0111011 | A1 | 5/2011 | Giovinazzo et al. |
| 2011/0287110 | A1 | 11/2011 | Dewhirst et al. |
| 2012/0009260 | A1 | 1/2012 | Schobel et al. |
| 2012/0071567 | A1 | 3/2012 | Crowley et al. |
| 2013/0273138 | A1 | 10/2013 | Serizawa |
| 2014/0046236 | A1 | 2/2014 | Filee et al. |
| 2014/0081070 | A1 | 3/2014 | Paukshto et al. |
| 2014/0234212 | A1 | 8/2014 | Goldberg et al. |
| 2015/0174076 | A1 | 6/2015 | Harris et al. |
| 2017/0239189 | A1 | 8/2017 | Goldberg et al. |
| 2017/0329189 | A1 | 11/2017 | Kim et al. |
| 2018/0154001 | A1 | 6/2018 | Dadey et al. |
| 2018/0169025 | A1 | 6/2018 | Goldberg et al. |
| 2018/0235899 | A1 | 8/2018 | Goldberg et al. |
| 2019/0142760 | A1 | 5/2019 | Goldberg et al. |
| 2019/0298799 | A1 | 10/2019 | Lichter et al. |
| 2019/0388356 | A1* | 12/2019 | Goldberg ............. A61K 31/282 |
| 2020/0078315 | A1 | 3/2020 | Goldberg et al. |
| 2020/0108072 | A1 | 4/2020 | Honigberg et al. |
| 2020/0306264 | A1 | 10/2020 | Surber |
| 2021/0087198 | A1 | 3/2021 | Rennie et al. |
| 2024/0099979 | A1 | 3/2024 | Goldberg |

FOREIGN PATENT DOCUMENTS

| | | | |
|---|---|---|---|
| DE | 10313427 | A1 | 1/2004 |
| EP | 0562864 | A1 | 9/1993 |
| EP | 1348830 | A2 | 10/2003 |
| JP | S6390507 | A | 4/1988 |
| KR | 200340228 | Y1 | 1/2004 |
| WO | 2005023323 | A1 | 3/2005 |
| WO | 2014130866 | A2 | 8/2014 |
| WO | 2017143294 | A1 | 8/2017 |
| WO | 2018151849 | A1 | 8/2018 |
| WO | 2021138646 | A1 | 7/2021 |

OTHER PUBLICATIONS

Clogston, J. et al., Zeta potential measurement, 2011, Methods Mol Biol., vol. 697, 63-70 (Abstract only) (Year: 2011).*

Amasya Gulin et al., “Bioadhesive and Mechanical Properties of Triamcinolone Acetonide Buccal Gels”, Journal of Pharmaceutical Sciences, 2012, 9(1), 1-12.

Derwent Abstract 1988-150559, Kibune et al. JP63090507A (Year: 2018).

U.S. Appl. No. 17/758,205 filed Jan. 3, 2021, Goldberg et al..

International Search Report and Written Opinion of PCT Application No. PCT/US2022/031790, mailed on Aug. 18, 2022, 9 pages.

International Search Report and Written Opinion received for PCT Application No. PCT/US2017/018514, mailed on Jul. 3, 2017, 10 pages.

International Search Report and Written Opinion received for PCT Application No. PCT/US2018/000065, mailed on May 28, 2018, 9 pages.

International Search Report and Written Opinion received for PCT Application No. PCT/US2014/017790 mailed on May 19, 2014, 12 pages.

Intraoperative Radiation Therapy (Jul. 20, 2018) WVU Medicine Health Report, West Virginia University; [https://www.cancercenter.com/treatments/intraoperative-radiation-therapy/]., 3 pages.

American Cancer Society (Mar. 8, 2017) “Causes, Risk Factors, and Prevention”, Colorectal Cancer Detailed guide, Retrieved from the Internet on Mar. 8, 2017:https://www.cancer.org/cancer/colon-rectal-cancer.html, 17 pages.

American Cancer Society (Jul. 23, 2018) “Understanding Advanced Cancer, Metastatic Cancer, and Bone Metastasis”, retrieved from the internet on Jul. 23, 2018 [https://www.cancer.org/treatment/understanding-your diagnosis/advanced-cancer/what-is . . . ], 8 pages.

American Cancer Society (Apr. 6, 2017) “What Is Melanoma Skin Cancer?”, Retrieved from the Internet on Apr. 6, 2017: http://www.cancer.org/cancer/skincancermelanoma/ detailedguide/melanoma-skincancerwhat-is-melanoma, 5 pages.

Barat et al. (2007) “Chitosan Inserts for Periodontitis: Influence of Drug Loading, Plasticizer and Crosslinking on In Vitro Metronidazole Release”, Acta Pharmaceutical, 57(4):469-477.

Barker et al (2008) “The Intestinal Stem Cell”, Genes & Development, 22(14):1856-1864.

Bhandri et al. (Aug. 6, 2012) “Nutrient Digestion and Absorption in the Gastrointestinal Tract”, Food Materials Science and Engineering, Section 8.2, 2 pages.

Cacciotti et al. (2014) “Effect of Silver Nanoparticles and Cellulose Nanocrystals on Electrospun Poly (Lactic) Acid Mats: Morphology, Thermal Properties and Mechanical Behavior”, Carbohydrate Polymers, 103:22-31.

Cancer Treatment Centers of America (Jul. 20, 2018) “Hyperthermic Intraperitoneal Chemotherapy (HIPEC)”, 2 pages.

Children’s Hospital of Pittsburg (Jul. 3, 2017) “Enema Administration”, Retrieved from the Internet on Mar. 7, 2017: http://www.chQ.edu/our-services/sugen:-pediatric/pediatric-surgery-services-we-offer/colorectalcenter-for-children/patient-family-resources/enemaadministration, 2 pages.

Cocoabio Tech. (Aug. 29, 2018) “Preparation and Use of a Dry Ice/Ethanol Bath”, Cited from the Internet: www.koko.gov/CocoaBioTech/ General%20Lab4.html, 2 pages.

Dai et al. (Jul. 2011) “Chitosan Preparations for Wounds and Burns: Antimicrobial and Would-Healing Effects”, Expert Review of Anti-infective Therapy, 7(9):857-879.

Defail et al. (2006) “Controlled Release of Bioactive TGF-Beta 1 From Microspheres Embedded Within Biodegradable Hydrogels”, Biomaterials, 27(8):1579-1585.

(56) References Cited

OTHER PUBLICATIONS

Dillekas et al. (2014) "Differences in Metastatic Patterns in Relation to Time Between Primary Surgery and First Relapse From Breast Cancer Suggest Synchronized Growth of Dormant Micrometastases", Breast Cancer Research and Treatment, 146(3):627-636.
Acrylic Adhesives and Acrylate Adhesives Information (2017) http://www.globalspec.com/learnmore/materials_chemicals/adhesives/acrylic_methacrylate_adhesives, accessed Nov. 6, 2 pages.
familydoctor.org (Jun. 4, 2017) "Burns: Preventing Burns in Your Home", First Aid: Burns: Retrieved from the Internet on Apr. 6, 2017: https://familydoctor.org/burns-preventingburns-in-your-home/, 3 pages.
Fight Colorectal Cancer (Jul. 3, 2017) "Managing Side Effects", http://fightcolorectalcancer.org/fight-it/managing-sideeffects/, 7 pages.
Galante et al. (Dec. 21, 2016) "About the Sterilization of Chitosan Hydrogel Nanoparticles", PLOS One, Article e0168862, 11(12):1-18.
Gillenwater et al. (Mar. 2006) "Oral Premalignancy: New Methods of Detection and Treatment", Current Oncology Reports, 8(2):146-154.
Gisbert et al. (2014) "Inflammatory Bowel Disease in the Elderly", Alimentary Pharmacology & Therapeutics, 39(5):459-477.
Glynne-Jones et al. (May 2010) "Anal Cancer: ESMO Clinical Practice Guidelines for Diagnosis, Treatment and Follow-up", Annals of Oncology, 21 (Suppl 5):v87-v92.
Goldberg et al. (Nov. 2014) "Development of a Nanoparticle-embedded Chitosan Sponge for Topical and Local Administration of Chemotherapeutic Agents", Journal of nanotechnology in engineering and medicine, 5(4):0409051-4090511(11 pages).
Gupta et al. (Jun. 2000) "Drug Release Behavior of Beads and Micro granules of Chitosan", Biomaterials, 21(11):1115-1119.
Hall D. (May 28, 2015) "The Three Phases of the Food Digestion Process", Retrieved from the Internet on Mar. 7, 2017: http://www.livestrong.com/article/312184-the-three-phases-of-the-food-digestion-process/.14 pages.
Hanauer et al. (Sep. 1998) "Budesonide Enema for the Treatment of Active, Distal Ulcerative Colitis and Proctitis: A Dose-Ranging Study", Gastroenterology, 115(3): 525-532.
Harless William W. (Apr. 22, 2009) "Revisiting perioperative chemotherapy: the critical importance of targeting residual cancer prior to wound healing", BMC Cancer, 9(18):9 pages.
Henderson R. ((Mar. 7, 2017)) "Prescribing for Children" Patient Platform Limited, [http://patient.info/doctor/prescribing-for-children]., 3 pages.
Hookman et al. (Apr. 7, 2009) "Clostridium Difficile Associated Infection, Diarrhea and Colitis", World Journal of Gastroenterology, 15(13):1554-1580.
Hwang et al. (2010) "Gentamicin-Loaded Wound Dressing With Polyvinyl Alcohol/Dextran Hydrogel: Gel Characterization and In Vivo Healing Evaluation", AAPS PharmSciTech, 11(3):1092-1103.
Ibrahim et al. (Oct. 2015) "Chitosan Nanoparticles Loaded Antibiotics as Drug Delivery Biomaterial", Journal of Applied Pharmaceutical Science, 5(10):085-090.
Jacobson et al. (2012) "The Cost Burden of Oral, Oral Pharyngeal, and Salivary Gland Cancers in Three Groups: Commercial Insurance, Medicare, and Medicaid", Head and Neck Oncology, 4(15):17 pages.
Ji et al. (2011) "Preparation, Characterization and in Vitro Release of Chitosan Nanopartides Loaded with Gentamicin and Salicylic Acid", Carbohydrate Polymers, 85(4):803-808.
Jonassen et al. (2012) "Stability of Chitosan Nanoparticles Cross-Linked with Tripolyphosphate", Biomacromolecules, 13(11):3747-3756.
Kann et al. (Apr. 5, 2017) "Burns: Types, Treatments, and More", Healthline Newsletter; http://www.healthline.com/health/burns?m=0#Overview1., 15 pages.
Kasper et al. (Jun. 2011) "The Freezing Step in Lyophilization: Physico-chemical Fundamentals, Freezing Methods and Consequences on Process Performance and Quality Attributes of Biopharmaceuticals", European Journal of Pharmaceutics and Biopharmaceutics, 78(2):248-263.
Koh et al. (2007) "A Systematic Review of the Function and Complications of Colonic Pouches", International Journal of Colorectal Disease, 22: 543-548.
Kotiyan et al. (2002) "Synthesis and Characterization of an Acrylate Pressure Sensitive Adhesive for Transdermal Drug Delivery", Polymers for Advanced Technologies, 13:137-143.
Kulkarnia et al. (Mar. 2001) "In-Vitro Release Kinetics of Cefadroxil-Loaded Sodium Alginate Interpenetrating Network Beads", European Journal of Pharmaceutics and Biopharmaceutics, 51(2):127-133.
Lai et al. (Feb. 27, 2009) "Mucus-Penetrating Nanoparticles for Drug and Gene Delivery to Mucosal Tissues", Advanced Drug Delivery Reviews, 61(2):158-171.
Laksitorini et al. (Oct. 2014) "Pathways and Progress in Improving Drug Delivery Through the Intestinal Mucosa and Blood-Brain Barriers", Therapeutic Delivery, 5(10):1143-1163.
Larkin Web (Aug. 29, 2018) "Lab Freezing Bath Temperatures", Cited from Internet: https://larkinweb.co.uk/science/freezing_bath temperatures.html, 3 pages.
Lee et al. (Jan. 18, 2016) "Controlled-Release of Tetracycline and Lovastatin by Poly (D,L-Lactide-Co-Glycolide Acid)-Chitosan Nanoparticles Enhances Periodontal Regeneration in Dogs", International Journal of Nanomedicine, 11:285-297.
Lee et al. (2004) "Effects of a Chitosan Scaffold Containing TGF-B1 Encapsulated Chitosan Microspheres on In Vitro Chondrocyte Culture", Artificial Organs, 28(9):829-839.
Lee et al. (Mar. 2001) "Equilibrium and Kinetic Studies of Copper (li) lon Uptake by Chitosan-tripolyphosphate Chelating Resin", Polymer, 42(5):1879-1892.
Li et al. (Feb. 2014) "Porous Chitosan Bilayer Membrane Containing TGF-B1 Loaded Microspheres for Pulp Capping and Reparative Dentin Formation in a Dog Model", Dental Materials, 30(2):172-181.
Liu et al. (Dec. 2008) "Polysaccharides-Based Nanoparticles as Drug Delivery Systems", Advanced Drug Delivery Reviews, 60(15):1650-1662.
Luangtana-Anan et al. (2005) "Effect of chitosan salts and molecular weight on a nanoparticulate carrier for therapeutic protein", Pharmaceutical Development and Technology, 10(2):189-196.
Macrae et al. (2017) "Clinical Presentation, Diagnosis, and Staging of Colorectal Cancer", UpToDate; Retrieved from the Internet on Mar. 8, 2017, http ://www.Uptodate.com/contents/clinical-Presentation-diagnosis-and-staging-of-colorectal-cancer, 20 pages.
Makarios-Laham et al., (1995), "Biodegradability of Chitin- and Chitosan-Containing Films in Soil Environment", Journal of Environmental Polymer Degradation, 3(1):31-36.
Maya et al. (Nov. 2012) "Efficacy of Tetracycline Encapsulated O-Carboxymethyl Chitosan Nanoparticles Against Intracellular Infections of *Staphylococcus aureus*", International Journal of Biological Macromolecules, 51(4):392-399.
Md Consult, (Aug. 3, 2017), "Anatomy and Histology of the Small and Large Intestine", Retrieved from the Internet on Mar. 8, 2017: http://jpck.zju.edu.cn/jcyxjp/files/ge/05/MT/0511.pdf, 18 pages.
Mi et al. (Mar. 2002) "Control of Wound Infections Using a Bilayer Chitosan Wound Dressing With Sustainable Antibiotic Delivery", Journal of Biomedical Materials Research, 59(3):438-449.
Misono et al., (Oct. 10, 2008), "Incidence of Suicide in Persons with Cancer", Journal of Clinical Oncology, Retrieved from the Internet on Mar. 9, 2017: http://jco.ascoQubs.org/content/26/29/4731.full, 26(29):4731-4738.
Miyazaki et al. (Jun. 2000) "Oral Mucosal Bioadhesive Tablets of Pectin and HPMC: In Vitro and In Vivo Evaluation", International Journal of Pharmaceutics, 204(1-2):127-132.
Mohandas et al. (Jun. 2015) "Drug Loaded Bi-Layered Sponge for Wound Management in Hyperfibrinolytic Conditions", Journal of Materials Chemistry B, 20(3):5795-5805.
Mulcahy et al. (Dec. 2012) "When Fighting Cancer Isn't Worth It", The Atlantic-Health, 5 pages.
Murata et al. (Sep. 2000) "Use of Floating Alginate Gel Beads for Stomach-specific Drug Delivery", European Journal of Pharmaceutics and Biopharmaceutics, 50(2):221-226.

(56) References Cited

OTHER PUBLICATIONS

Nagpal et al. (Nov. 2010) "Chitosan Nanoparticles: A Promising System in Novel Drug Delivery", Chemical and Pharmaceutical Bulletin, 58(11): 1423-1430.
National Cancer Institute (2018) "Metastatic Cancer, What Is Metastatic Cancer?", retrieved from internet on Jul. 20, 2018., 5 pages.
National Cancer Institute (2017) "Surveillance, Epidemiology, and End Result Program (SEER)", Cancer of the Anus, Anal Canal, and Anorectum—Cancer Stat Facts Retrieved from the Internet on Mar. 7, 2017: https://seer.cancer.gov/statfacts/html/anus.html, 9 pages.
National Psoriasis Foundation (2017) "50 Years Driving Discovery, Creating Community", retrieved from the internet on Apr. 5, 2017 [https://www.psoriasis.org/], 4 pages.
National Psoriasis Foundation (2017) "Causes and Triggers", Retrieved from the Internet on Apr. 6, 2017. https://www.psoriasis.org/ about psoriasis/ causes, 6 pages.
National Psoriasis Foundation (2017) "Psoriasis Foundation", Retrieved from the Internet on Apr. 6, 2017. https://www.psoriasis.org/, 1 page.
New Radiant Technology S.P.A. (2018) "Novac 7, The first mobile electron linear accelerator for IORT", retrieved from the internet on Jul. 20, 2018 [http://sennewald.de/wp-content/uploads/novac7.pdf]., 6 pages.
Dr. Colin Trudy (2017) "Prescribing for Children", Patient Platform Limited Retrieved from the Internet on Mar. 7, 2017: http://patient.info/doctor/prescribing-for-children, 3 pages.
Patapoff et al. (Mar. 15, 2002) "The Importance of Freezing on Lyophilization Cycle Development", BioPharm International, 15(3):16-22,72.
Patil et al. (2012) "A Review on lonotropic Gelation Method: Novel Approach for Controlled Gastroretentive Gelispheres", International Journal of Pharmacy and Pharmaceutical Sciences, 4(4):27-32.
Paun et al. (2010) "Postoperative Complications Following Surgery for Rectal Cancer", Annals of Surgery, 251(5): 807-818.
Rodriguez-Arguelles et al. (Dec. 2011) "Chitosan and Silver Nanoparticles as Pudding with Raisins with Antimicrobial Properties", Journal of Colloid and Interface Science, 364(1):80-84.
Ryan et al. (2017) "Clinical Features, Staging, and Treatment of Anal Cancer", Retrieved from the Internet on Mar. 8, 2017; https://www.uptodate.com/contents/clinical-features-and-staging-of-anal-cancer, 10 pages.
Saramento et al. (Mar. 2012) "Chitosan-Based Systems for Biopharmaceuticals: Delivery, Targeting and Polymer Therapeutics", John Wiley & Son, Ltd, 564 pages.
Shaw D et al. (Nov. 28, 2012) "The Intestinal Mucosal Atrophy and Adaptation", World Journal of Gastroenterology, 18(44):6357-6375.
Sigma-Aldrich (Apr. 2007) "Hanks' Balanced Salts [HBSS]", Retrieved from Internet: https://www.sigmaaldrich.com/content/dam/sigmaaldrich/docs/ . . . /1/hl387pis.pdf; 1 page.
Sperk et al. (2014) "A Cohort Analysis to Identify Eligible Patients for Intraoperative Radiotherapy (IORT) of Early Breast Cancer", Radiation Oncology, 9(154):7 pages.
The HPV and Anal Cancer Foundation (2017) "Living with Anal Cancer—Causes & Risk Factors", Retrieved from the Internet on Mar. 7, 2017: http://www.analcancerfoundation.org/living-with-anal-cancer/anal-cancer-risk-factors-causes/, 8 pages.
The HPV and Anal Cancer Foundation (2017) "Living with Anal Cancer/Treatment for Anal Cancer", Retrieved from the Internet on Mar. 8, 2017. http://www.analcancerfoundation.org/living-with-analcancer/anal-cancer-treatment/, 18 pages.
The Oral Cancer Foundation (2017) "Information-Support-Advocacy Research . . . and Hope", Retrieved from the Internet on Mar. 9, 2017. http://oralcancerfoundation.org/, 3 pages.
The Oral Cancer Foundation (2017) "Mucositis", Retrieved from the Internet on Mar. 9, 2017. http://oralcancerfoundation.org/comQlications/mucositis/, 14 pages.
Tufts Medical Center (2018) "Cytoreductive Surgery with Hyperthermic Intraperitoneal Chemotherapy (HIPEC)", FAQ's, retrieved from the internet on Jul. 20, 2018, 7 pages.
Tulunay et al. (Mar. 2007) "Pilot Study of Intraoperative Chemotherapy With Cisplatin and 5-Fluorouracil in Patients With Advanced Squamous Cell Carcinoma of the Head And Neck", Head Neck, 29(3):267-271.
Weinberg et al. (Apr. 1, 2002) "Assessing Oral Malignancies", American Family Physician, 65(7):1379-1384.
Weng et al. (2016) "Burns: Types, Treatments, and More", Healthline Newsletter; Retrieved from the Internet on Apr. 5, 2017. http://www.healthline.com/health/burns?m=O#Overview1 Information, 15 pages.
Willett et al. (2017) "Adjuvant Therapy for Resected Rectal Adenocarcinoma", Retrieved from the Internet on Mar. 8, 2017. http://www.UQtodate.com/ contents/ adjuvant-theram:-forresected-rectal-adenocarcinoma, 5 pages.
Youssef et al. (Apr. 2002) "Management of Intractable Constipation With Antegrade Enemas in Neurologically Intact Children", Journal of Pediatric Gastroenterology & Nutrition, 34(4):402-405.
Zhang et al. (2013) "Effect of Chitosan and Carboxymethyl Chitosan on Fibrinogen Structure and Blood Coagulation", Journal of Biomaterials Science, Polymer Edition, 24(13):1549-1563.
Zhang et al. (2004) "Monodisperse Chitosan Nanoparticles for Mucosal Drug Delivery", Biomacromolecules, 5(6):2461-2468.
Zhang et al. (May/Jun. 2013) "Polymeric Nanoparticles-Based Topical Delivery Systems for the Treatment of Dermatological Diseases", Nanomedicine and Nanobiotechnology, 5(3):205-218.
Xu, Q. et al., "Prevention of colorectal cancer liver metastasis by exploiting liver immunity via chitosan-TPP/nanoparticles formulated with IL-12" Biomaterials, 33(15):3909-3918, May 2012.
Ayensu et al., "Effect of membrane dialysis on characteristics of lyophilised chitosan wafers for potential buccal delivery of proteins" Intl J. Biological Macromolecules 50:905-909, 2012.

* cited by examiner

ENHANCED TWO-STAGE MICROPARTICLE-BASED LOCALIZED THERAPEUTIC DELIVERY SYSTEM

CROSS-REFERENCES TO RELATED APPLICATIONS

This application claims priority to U.S. Provisional Application No. 63/195,469, filed Jun. 1, 2021, which is incorporated herein by reference in its entirety for all purposes.

BACKGROUND OF THE INVENTION

Cancers affecting the mucosae of the body are a growing public health concern. Oral cancer alone affects over 640,000 people annually worldwide and over 40,000 in the US. The incidence is on the rise due to an increased affliction with oral HPV, which is cancer causing. Treatment methods include surgery and systemic chemotherapy administered intravenously, often in combination. Surgery is often ineffective due to the difficulty associated with identifying margins surrounding oral tumors. This inability to completely remove tumors during surgery contributes to oral cancer's high rate of recurrence. Systemic chemotherapy is often used but lacks targeting and exposes the patient's entire body to damaging chemotherapeutics. This method can be dose limiting due to exposure within the blood stream and other organs, as precautions must be taken in consideration of the safety of this systemic exposure. Systemic delivery often results in damaging side effects from toxic drugs reacting with the body. These include neurotoxicity, nephrotoxicity, kidney failure, hair loss, nausea and mucositis.

In addition, oral cancer is among the most debilitating diseases. Permanent disfiguration can occur after surgical resection of oral tumors. The patient's ability to eat, drink, or properly speak after surgery can also become impaired or not possible. In part for these reasons, oral cancer is considered the most expensive cancer to treat.

The emotional side effects also speak to the especially tragic and debilitating effect of oral cancer compared to other cancers and diseases. The emotional toll on oral cancer patients can be far greater than that of other diseases, primarily due to the physical deformity (including physical appearance and lack of clear speech) that results from treatment. These consequences of traditional treatment methods for oral cancer illustrate why an alternative treatment method is desperately needed to address this unmet need and patient suffering.

Anal cancer accounts for 2.5 percentage of all digestive system malignances in the US, and approximately 8,000 new cases are diagnosed annually. The incidence of anal cancer in the general population has increased over the last three decades. Additionally, colorectal cancer (CRC) is a common and lethal disease. It is estimated that approximately 134,490 new cases of large bowel cancer are diagnosed annually in the US, including approximately 95,270 colon and 39,220 rectal cancers. This cancer remains the third most common cause of cancer death in the United States. Approximately 49,190 Americans are expected to die of large bowel cancer each year.

One of the differences between colorectal cancer and anal cancer are the risk factors that can cause each. Primary risk factors for colorectal cancer include age, genetics, race, diabetes, obesity, lack of exercise and smoking. In contrast, the primary cause of anal cancer has been the increase in prevalence of human papillomavirus (HPV).

These cancers, oral, colorectal and anal cancer, can all be treated with cisplatin, a platinum-containing drug with widespread anti-tumor activity. This drug is an alkylation agent, used for treating solid tumors such as testicular, ovarian, bladder and epithelial malignancies and cancers of the esophagus, lung, and head and neck. Following entry into the target cells via diffusion, the substitution of water for one or more chlorine atoms gives it a positive charge, with the resulting positively charged complex reacting with DNA to inhibit DNA replication. This property of cisplatin, however, makes it prone to hydrolysis. The addition of sodium chloride can mitigate this risk by improving the chemical stability of cisplatin. Improved methods of delivering cisplatin to treat oral, anal and colorectal cancers are needed. The present invention meets this and other needs.

BRIEF SUMMARY OF THE INVENTION

In one embodiment, the present invention provides a system for delivery of cisplatin to a site in mucosal tissue, the system comprising a porous, mucoadhesive, freeze-dried polymeric matrix, having first and second opposed surfaces, the matrix formed by a composition including chitosan in an aqueous solution of a chloride salt of a monovalent cation, the chloride salt having a concentration of between about 10 wt % and about 18 wt %; and a plurality of microparticles, the microparticles comprising chitosan and having an average diameter between 500 nm and 2000 nm, the microparticles being embedded within the matrix so as to be directly surrounded by, and in contact with, the matrix, the microparticles containing cisplatin. In this embodiment, (i) the first surface of the matrix is configured to attach to the site in the mucosal tissue; (ii) the matrix is configured to provide controlled release of the microparticles, through the first surface, when the first surface of the matrix is thus attached to the site; and (iii) the microparticles are configured so as to provide controlled release of the cisplatin.

In another embodiment, the present invention provides a system comprising: a polymeric matrix comprising chitosan, and a plurality of microparticles each comprising chitosan, a chloride salt of a monovalent cation having a concentration of from about 10 to about 18% (w/w) of the polymeric matrix, and a therapeutic agent, wherein the microparticles have an average diameter between 500 nm and 2000 nm.

In another embodiment, the chloride salt of a monovalent cation is chosen from the group consisting of NaCl, KCl, LiCl, RbCl, CsCl, NH4Cl, and combinations thereof. Optionally, the chloride salt of a monovalent cation is NaCl. Also optionally, the aqueous solution of a chloride salt of a monovalent cation includes propylene glycol in a concentration of from about 5 weight percent to about 25 weight percent. As a further option, the aqueous solution of a chloride salt of a monovalent cation includes hydroxypropylmethylcellulose (HPMC) in a concentration of from about 0.1 weight percent to about 10 weight percent. In yet another related embodiment, the aqueous solution of a chloride salt of a monovalent cation includes sucralose in a concentration of from about 0.1 weight percent to about 30 weight percent. In a further related embodiment, the microparticles are present in the matrix in a concentration of about 10 to about 40 weight percent. Optionally, the system further includes a water-permeable backing layer applied to the matrix.

In another embodiment, the present invention provides a method of administering a therapeutic agent to a subject in need thereof, comprising applying a system of the present invention to the subject such that at least 50% of a therapeutic agent of the system is released from the system in less than 30 minutes.

In another embodiment, the present invention provides a method of preparing the system of the present invention, comprising forming a first mixture comprising water, chitosan, a chloride salt, a hydration promoter, a particle adhesion inhibitor, and a microparticle aggregation inhibitor, to prepare a matrix mixture;

forming a second mixture comprising the matrix mixture, a first platinum antineoplastic agent, and chitosan microparticles comprising a second platinum antineoplastic agent;

removing the water from the second mixture, to prepare a dried mixture; and applying the dried mixture to a backing layer, thereby preparing the system.

In another embodiment, the present invention provides a method of preparing a system of the present invention, comprising:

forming a first mixture comprising water, chitosan, and acetic acid;

forming a second mixture comprising a chloride salt, a therapeutic agent, and sodium tripolyphosphate;

forming a third mixture comprising the first mixture and the second mixture, thereby forming microparticles;

forming a fourth mixture comprising water, chitosan, acetic acid, a hydration promoter, and a particle adhesion inhibitor;

forming a fifth mixture comprising the fourth mixture, a particle aggregation inhibitor, and the microparticles, to form the polymer matrix;

removing the water from the polymer matrix, to prepare a dried mixture; and applying the dried mixture to a backing layer, thereby preparing a system of the present invention.

In another embodiment, the present invention provides a method of treating a skin disease of a subject in need thereof, comprising applying a system of the present invention to the skin of the subject such that a therapeutically effective amount of a therapeutic agent of the system is released from the system and administered to the skin of the subject, thereby treating the skin disease.

In another embodiment, the present invention provides a method of treating a mucosal cancer, comprising applying the system of the present invention to the mucosal cancer of a subject in need thereof, thereby treating the mucosal cancer.

BRIEF DESCRIPTION OF THE DRAWINGS

The foregoing features of embodiments will be more readily understood by reference to the following detailed description, taken with reference to the accompanying drawings, in which:

FIG. 8A is a photograph showing application of a patch to the buccal mucosa, and FIG. 8B is a photograph showing application of a patch to a mucosal lesion on the anterior two-thirds of the tongue.

FIG. 12A shows the untreated patient.

FIG. 12B shows the patient after 3 treatments. FIG. 12C shows the patient after 6 treatments.

DETAILED DESCRIPTION OF THE INVENTION

I. General

Figure 1:
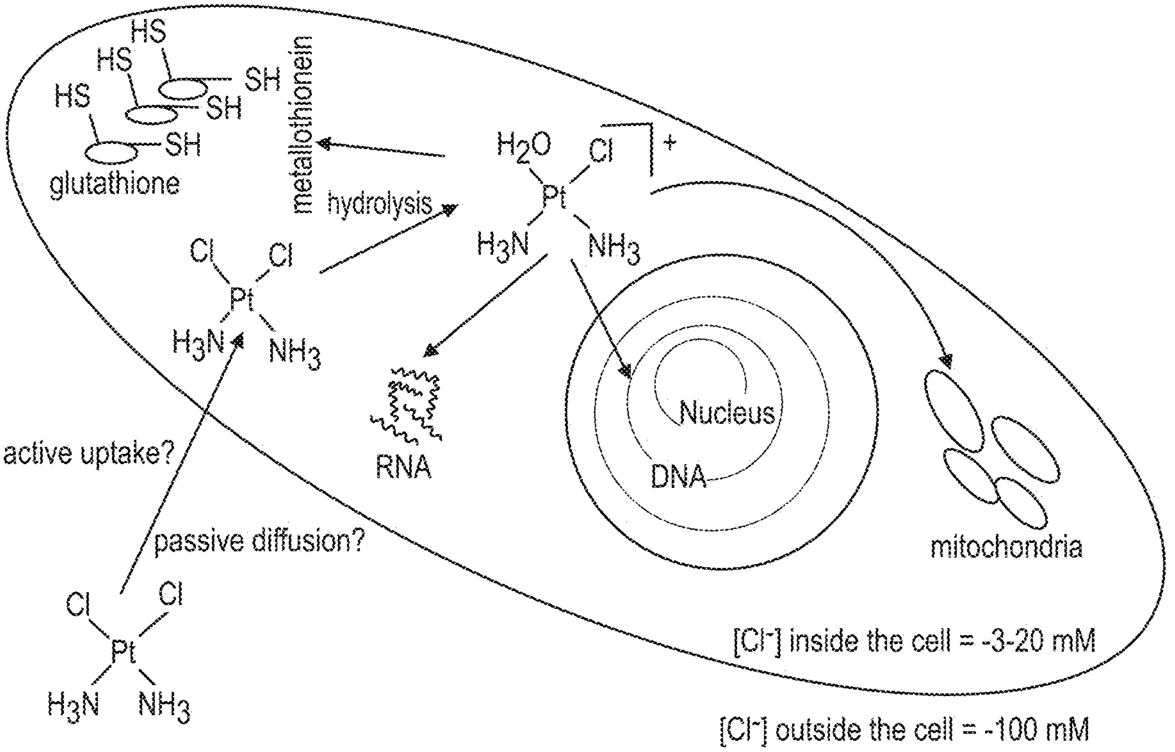
FIG. 1 is a diagram showing how the presence of sodium chloride in solution with cisplatin has been known in the prior art to improve the stability of cisplatin as an anti-cancer therapeutic by avoiding premature hydrolysis outside of the cell. Once the stable cisplatin (enters the cell membrane, then the hydrolysis inside the cell allows for the DNA damage and cell necrosis as shown above.

The present disclosure describes patches for the treatment of skin diseases and mucosal cancers using a therapeutic agent delivered from a patch containing about 18% w/w of sodium chloride.

II. Definitions

As used in this description and the accompanying claims, the following terms shall have the meanings indicated, unless the context otherwise requires:

A "set" includes at least one member.

"Microparticles" are sets of particles having an average diameter of at least 200 nm to at most 2000 nm.

"Nanoparticles" are sets of particles having an average diameter of at least 1 nm to below 200 nm.

"Matrix" refers to a polymer matrix composed primarily of a polysaccharide polymer. The matrix can be a porous matrix, wherein a fraction of its volume is void space. In some instances, the void space is accessible from the outer surface of the matrix, so that items present in the void space, such as microparticles, may migrate to and from the outer surface.

"Mucoadhesive" refers to a material characterized as having the ability to adhere to mucosal membranes in the human body.

"Chitosan" refers to a polysaccharide of beta-1,4-D-glucosamine and N-acetyl-D-glucosamine with an average molecular weight of about 3.8 to 20 kDa. "Pure chitosan" is a chitosan that is not a salt of chitosan.

"Chloride salt" refers to an organic or inorganic salt having a chloride anion. Representative chloride salts include sodium chloride and potassium chloride.

"Monovalent cation" refers to a positively charged ion with a valence capable of forming one covalent bond. Examples include alkali metals (sodium, potassium, etc.), ammonium, quaternary ammonium or the like.

"Hydration promoter" refers to an additive that increases moisture absorption, and acts as a cryoprotectant during the manufacturing process.

"Particle adhesion inhibitor" refers to an additive that lowers the attractive forces between a polymeric matrix and particles embedded therein. As a result, the particles can move through the matrix at a faster rate than in the absence of the adhesion inhibitor.

"Polydispersity index" (PDI) or simply, "dispersity" is used herein to refer to a measure of the heterogeneity of sizes of particles in a mixture. PDI measures the size dispersity of nanoparticles.

"Zeta potential" (ZP) is used herein to refer to the overall charge that particles acquire in a particular medium and can be measured on a Zetasizer Nano instrument.

"Particle diameter" is the length of the longest axis between two points on the surface of the particle.

"Biocompatible" refers to the ability of a biomaterial to perform its desired function with respect to a medical therapy, without eliciting any significant undesirable local or systemic effects in the recipient or beneficiary of that therapy, but generating the most appropriate beneficial cellular or tissue response in that specific situation, and optimizing the clinically relevant performance of that therapy.

"Hydroxypropylmethylcellulose" (HPMC) refers to the non-ionic polymer represented by the structure below:

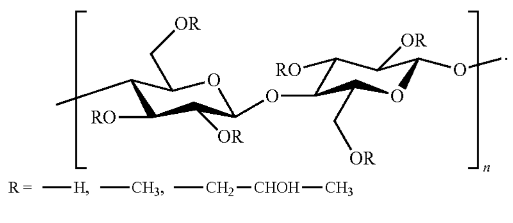

"Biodegradable" refers to a property of the materials that is capable of being broken down especially into innocuous products by the action of living things.

"Tissue" in the context of embodiments of the present invention refers to organ, epithelial, mucosal, or other tissue which exists within regions such as the abdomen, pelvis, intraperitoneal cavity, and/or other intraperitoneal surfaces.

"Surgical cavity" refers to the cavity, opening, site or tissue surface that results from the surgical resection of tissue.

"Rapid", "rapid release", or "rapid delivery" in reference to release from the patch refers to the release of between 20% and 100% of the patch's payload within approximately 20 minutes.

"Kilo counts per second" or "Kcps", mean count rate (in thousands of counts per second). For example, the threshold may be set such that when the count rate of the sample is lower than 100, the measurement should be aborted, meaning the concentration of the sample is too low for measurements. A sample with suitable Kcps can be considered a stable sample with an acceptable concentration for measurement.

"Mesh" refers to a device, sponge, wafer, or like product which contains elements incorporated within it to be released from the mesh when it is applied to a mucosa.

"System for delivery of a therapeutic agent based on a polymeric matrix and microparticles" may also be referred to as an "agent delivery device" or as a "delivery patch".

Unless otherwise specified, the term "wt %" or "% (w/w)" refers to the amount of a component of a system for delivery of a therapeutic agent, as expressed in percentage by weight.

Unless otherwise specified, the "molar mass" of a polymer is intended to mean the number average molar mass of the polymer molecules.

"Particle aggregation inhibitor" refers to an additive that lowers the tendency of particles embedded in a matrix to aggregate when the matrix is subjected to freezing. As a result, the particles are less likely to suffer from damage or destruction when the freezing takes place.

"Monosaccharide" refers to the simplest form of sugar which constitutes the building blocks of more complex forms of sugar. Representative compounds include glucose, fructose, and galactose.

"Disaccharide" refers to the sugar compounds comprising two monosaccharides joined by a glycosidic linkage. Representative compounds includes sucrose, lactose, and maltose.

"Sugar alcohol" refers to a compound produced by the reduction of a sugar compound to an alcohol.

"Chlorinated monosaccharide" refers to a monosaccharide compound substituted by at least one chlorine atom.

"Chlorinated disaccharide" refers to a disaccharide compound substituted by at least one chlorine atom.

"Sucralose" refers to the chlorinated disaccharide represented by the structure below:

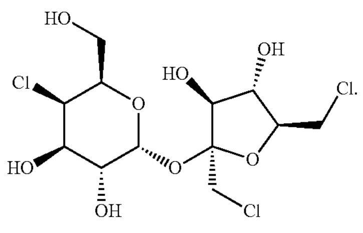 [SMILES: OC[C@H]1O[C@H](O[C@]2(CCl)O[C@H](CCl)[C@@H](O)[C@@H]2O)[C@H](O)[C@@H](O)[C@H]1Cl]

"Embedded within the matrix" refers to the state or configuration of one or more particles in which one or more particles are directly surrounded by, and in contact with a matrix.

"Directly surrounded by, and in contact with" refers to the state or configuration of one or more particles which are encapsulated or trapped with another substance or material (e.g., a matrix) such the entire outermost layer of the one or more particles is in direct contact with the surrounding material.

"Sodium tripolyphosphate" refers to the compound represented by the structure below:

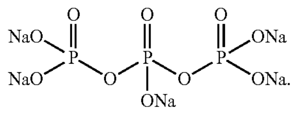

"Water-permeable backing layer" refers to a material that is permeable, or at least substantially permeable to, the passage of water.

"Surface" refers to a particular area or site on a particle which is considered to be the outermost portion of the particle. The surface may refer to the area or site whereby a particle contains reactive sites or reactive species capable of interacting with its surroundings. A surface of a particle may also function as a barrier to one or more layers underneath or surrounded by the outermost layer.

"Polyacrylate adhesive" refers to an adhesive material made from polyacrylate (acrylic polymers), such as those made from monomeric esters (e.g., acrylic acid and methacrylic acid). Examples of polyacrylate-based adhesives are as follows, identified as product numbers, manufactured by National Starch (Product Bulletin, 2000, DURO-TAK.RTM. is a trademark of National Starch adhesives): 87-4098, 87-2287, 87-4287, 87-2516, 87-2051, 87-2052, 87-2054, 87-2196, 87-9259, 87-9261, 87-2979, 87-2510, 87-2353, 87-2100, 87-2852, 87-2074, 87-2258, 87-9085, 87-9301 and 87-5298.

"Non-woven polyester fabric" refers to a textile made from a random collection of fibers of polyester. The fibers generally can be bonded to each other or can be unbonded, and can be staple fibers or continuous fibers.

"Treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom.

"Mucosal tissue" refers to a tissue having an associated mucosa. In particular, mucosal tissue includes the mucosa and also tissue underlying the mucosa. A "site in mucosal tissue", where, for example, a cancerous tumor is present may involve not only the mucosa but also tissue underlying the mucosa. Representative mucosal tissue includes the oral cavity.

"Mucosal cancer" refers to a cancer of the mucosal cells, and includes oral cancer, nasopharyngeal carcinoma, tongue cancer, gastrointestinal cancer, colorectal cancer, anal cancer, and laryngeal carcinoma.

"Tumor" refers to all neoplastic cell growth and proliferation, whether malignant or benign, and all pre-cancerous and cancerous cells and tissues. "Neoplastic" as used herein, refers to any form of dysregulated or unregulated cell growth, whether malignant or benign, resulting in abnormal tissue growth. Thus, "neoplastic cells" include malignant and benign cells having dysregulated or unregulated cell growth.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

"Subject" or "patient" refers to animals such as mammals, including, but not limited to, primates (e.g., humans), cows, sheep, goats, horses, dogs, cats, rabbits, rats, mice and the like. In certain embodiments, the subject is a human.

"Therapeutic agent" refers to a compound, peptide, antibody, or cell, that is useful and effective to treat a disease or disorder such as a skin disease.

"Release", "released" or "releasing" refers to the movement of a therapeutic agent from a patch of the present invention and to the subject or patient.

"Skin disease" refers to an affliction or disease manifesting itself primarily in the skin of a subject.

"Mucosal cancer" refers to a cancer that manifests itself primarily in a mucosal membrane, such as, but not limited to, the oral cavity, vagina and rectum.

III. Systems

The device or systems of the present invention includes agent-encapsulating particles consisting of a polymer having dispersed or encapsulating therein a therapeutic, prophylactic, diagnostic or nutraceutical agent. If desired, the particles may include chemical linkers, which can couple targeting ligands and/or additional agents to the particles. The device includes these particles as well as preferably permeation enhancers.

The device or systems may be orally administered via tablet, capsule, liquid, syrup, gelatin or other oral consumable, or via nasogastric tube or feeding tube for those who are unable to swallow, and exhibits properties which allow the agent encapsulated in the particles to remain stable in the variably acidic environment of the stomach. The device is able to deliver agent-encapsulated particles ("loaded particles", also labeled as "LPs") to the epithelial cells within the gastrointestinal (GI) tract. The particles adhere to the intestinal mucosa and degrade, releasing the encapsulated agent directly into the intestinal epithelium.

The particles (preferably having an average diameter of 500 to 2000 nanometers (nm)) permeate the mucosal tissue of the intestine. This size is adequate to carry enough therapeutic, diagnostic or nutraceutical agent to obtain high loading and encapsulation efficiencies (higher than 80%), which is desirable for scaling up and commercialization.

The encapsulation of therapeutic, diagnostic and/or nutraceutical agents allows for controlled penetration into the mucus, by means of adding a targeting ligand, as well as a controlled release profile. Moreover, in the case of systemic penetration, the encapsulation also reduces uptake by the body's reticuloendothelial system. The smaller particles have greater surface area-to-volume ratios, which cause the particles' dissolution rates to be higher than that of larger particles.

Many agents are limited in delivery due to solubility factors. The large surface area to volume of particles increases the bioadhesivity. These factors in combination result in the penetration of the agent deep into ISCs, providing a greater benefit.

There are three main aspects of targeting that work to achieve localized delivery:

1. Charge: Positively charged polymers may be used in the synthesis of the particles included in this delivery system. The resulting device exhibits a positive charge which attracts the agent-encapsulated particles to the negatively charged mucosa of the intestine.
2. Activity: Obtained using molecular targeting agents to further focus on intestinal stem cells (ISCs).
3. pH: Particles in the present compositions are able to be modified to remain stable or release agents in varying pH environments. This determination takes place during the synthesis process. By synthesizing particles which keep the agent encapsulated in the highly acidic environment of the stomach and promote release in the more basic environment of the intestines, release is therefore targeted. These parameters can be changed to include release in more acidic environments or combinations thereof. These parameters can also be changed to allow for release in both the stomach and intestines. Further, varying doses and varying drug combinations are also possible. FIG. 22C shows an example of particles which release as the pH approaches neutral levels.

The present disclosure describes patches for the treatment of oral cancers using a platinum antineoplastic agent stabilized using about 18% w/w of sodium chloride in the patch.

In some embodiments, the present invention provides a system comprising: a polymeric matrix comprising chitosan, and a plurality of microparticles each comprising chitosan, a chloride salt of a monovalent cation having a concentration of from about 10 to about 18% (w/w) of the polymeric matrix, and a therapeutic agent, wherein the microparticles have an average diameter between 500 nm and 2000 nm.

Figure 10:
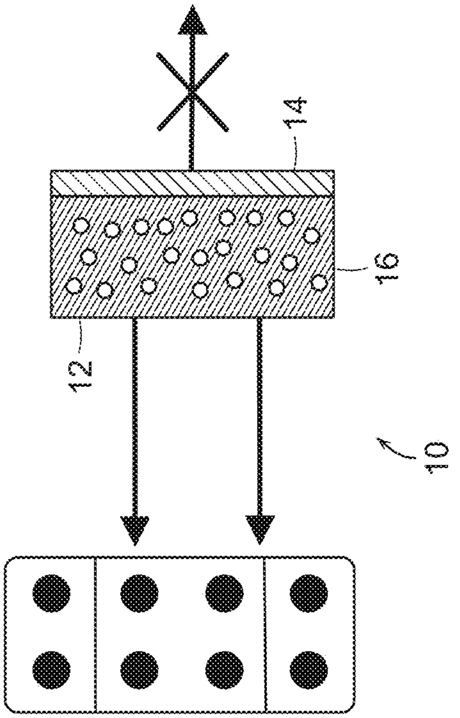
FIG. 10 shows a patch 10 includes a layer 12 having first and second opposed surfaces and a backing layer 14 adjacent to one of the surfaces.

As illustrated in FIG. 10, a patch 10 includes a layer 12 having first and second opposed surfaces and a backing layer 14 adjacent to one of the surfaces. Layer 12 contains at least one therapeutic agent and a porous, mucoadhesive polymeric matrix that is formed by freeze-drying a composition including chitosan. Particles 16 are embedded within the matrix. The particles are directly surrounded by, and in contact with, the matrix. The particles contain the therapeutic agent and have a coating around the therapeutic agent, the coating including chitosan so as to provide controlled release of the therapeutic agent from the particles. A quantity of the therapeutic agent may be embedded directly in the matrix as freeform agent, and not otherwise coated with chitosan. In representative examples, the freeform quantity of the therapeutic agent constitutes between 20-80% of a total quantity of the therapeutic agent in the device. Backing layer 14 is impermeable to, or at least substantially impermeable to, the passage of one or more payload components such as the particles, therapeutic agent, or additives present in the patch. Examples of backing layer materials include a non-woven polyester fabric with or without a polyacrylate adhesive and/or a clear acrylic film.

Figure 8:
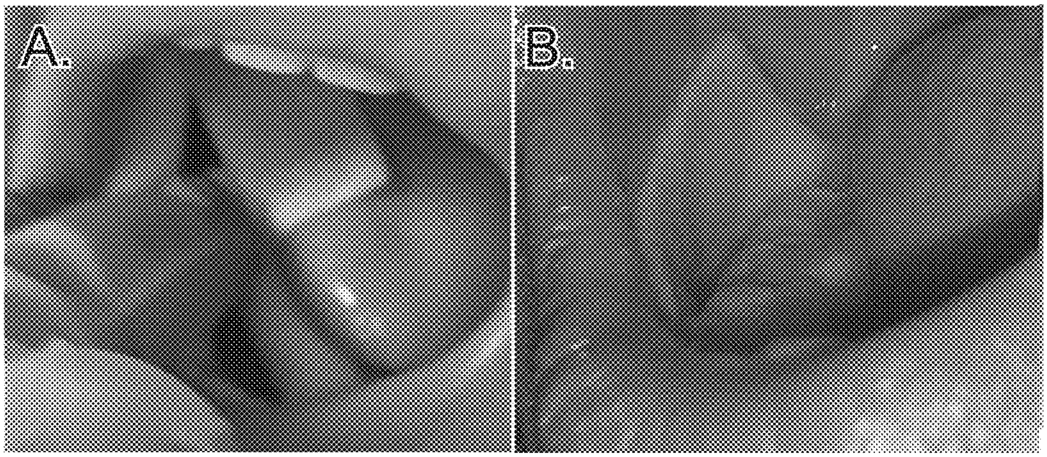
FIGS. 8A and 8B show application of the patch to the buccal mucosa.

In some embodiments, the patch is formed with one side exposed for contact with the appropriate tissue. Particles containing the agent or agents will be released from this side upon contact with the appropriate tissue. As illustrated in FIG. 8 the particles (round) are held within the body of the patch. The body of the patch is the web-like material, which is primarily comprised of chitosan. In some embodiments, the other side facing the external cavity may be adjacent to a backing layer 14, for instance a film, coating, or impermeable membrane to prevent significant loss of one or more payload components from the patch into the tissue/cavity on the opposite side from the desired tissue. This backing layer 14 may also prevent contamination of the patch with fluids or other matter that may be present.

Matrix

Several bioadhesive and mucoadhesive polymers are known. In some embodiments, the polymer is mucoadhesive so that it can bind to the mucosal intestinal tissue. In some embodiments, the polymer is polycationic, biocompatible, and biodegradable. In some embodiments, the polymer is chitosan. Chitosan is a polycationic, non-toxic, biocompatible and biodegradable polymer. Chitosan is commonly used as a mucosal agent delivery mechanism because of its bio-adhesiveness and permeability properties. The barrier in GI epithelium can easily be disrupted by chitosan particles, enhancing permeability through the mucosa.

Different factors affect fabrication of chitosan particles, such as pH of the preparation, inclusion of polyanions, charge ratios, the degree of deacetylation and the molecular weight of chitosan.

Chitosan particles have, to date, been demonstrated for use with chemotherapeutics for cancer treatment because of the chitosan's sensitivity to low pH. Since cancer tissue is acidic, chitosan particles release the agent faster in an acidic environment. However, in contrast to traditional uses of chitosan particles, provided herein is a new chitosan particle synthesis process to allow for stability in acidic environments and agent release when exposed to basic conditions. The controlled release of the agent from the chitosan particles ensures that a steady amount of agent penetrates the proper GI mucosal tissue while minimizing loss and exposure to fluids and other tissue.

The system can include any suitable polymeric matrix. In some embodiments, the polymeric matrix is a porous, mucoadhesive, freeze-dried polymer matrix. Representative polymer matrices useful as the polymer matrix include, but are not limited to, chitosan. The chitosan can be pure chitosan, or a salt of chitosan. In some embodiments, the chitosan is pure chitosan. The chitosan can be any suitable molecular weight, such as from about 25 kDa to about 1000 kDa, or about 25 kDa to about 500 KDa, or about 50 kDa to about 500 kDa, or about 50 kDa to about 250 kDa, or about 80 kDa to about 200 kDa. In some embodiments, the chitosan has a molecular weight of from about 25 kDa to 1000 kDa. In some embodiments, the chitosan has a molecular weight of from about 25 kDa to 500 kDa. In some embodiments, the chitosan has a molecular weight of from about 80 kDa to 200 kDa.

Representative examples of matrix materials and particles that can form layer 12 are provided in U.S. Patent Appl. Publ. No. 2017/0239189, where chitosan particles embedded in a chitosan-based matrix are disclosed. Chitosan is a deacetylated derivative of chitin, the second most abundant polysaccharide, and has a large density of reactive groups and a wide range of molecular weights. Chitosan is considered useful as a bioadhesive material because of its ability to form non-covalent bonds with biological tissues, mainly epithelia and mucous membranes. Bioadhesions formed using natural polymers have unique properties as a carrier because they can prolong residence time and, therefore, increase the absorbance of loaded drugs. Chitosan is a bioabsorbable, biocompatible, biodegradable, anti-bacterial and non-toxic polymer.

In addition, chitosan has different functional groups that can be modified. Because of its unique physicochemical properties, chitosan has great potential in a range of biomedical applications. Chitosan can be used as a delivery mechanism because of its bio-adhesiveness as well as its established ability to act as an absorption and permeation enhancer. The barrier in mucosa or epithelium can easily be disrupted by chitosan particles, enhancing permeability through mucosa. Chitosan has been found to be an ideal material for enabling efficacy and functionality of the patch. In the course of experiments, following surgical resection of tumors, a chitosan-based patch was applied within the surgical cavity. Only treatment with the chitosan-based patch resulted in essentially no recurrence or metastasis of cancer cells. Other patches, such as patches made of purely HPMC, pectin, alginate did not yield these same effects for unknown reasons. Chitosan is a blood coagulant, likely due to chitosan's positive charge attracting and retaining negatively-charged red blood cells upon exposure to blood, which results in coagulation. This coagulation, in combination with other unknown factors, may prevent the spread of free cancer cells within the bloodstream and body. In addition, chitosan loosens the tight cell junctions within tissue to increase permeation and passage of agents within tissue. This effect may, in part, prevent the spread of cancerous cells within local and systemic tissue due to cancerous cells becoming attracted towards the patch because of the cells' more acidic properties or other unknown factors. In permeation studies conducted with a number of patch materials, similar permeation of particles was noted in chitosan-based patches as well as non-chitosan-based patches, so additional permeation, in and of itself, does not result in this higher efficacy.

The most widely developed particle manufacturing methods are ionotropic gelation and self-assembling polyelectrolytes. These methods offer many advantages, such as a simple and mild preparation method without the use of organic solvent or high shear force. These methods are applicable to broad categories of agents including macromolecules which are notorious as labile agents. Usually, the factors found that affects particle formation, including particle size and surface charge, are molecular weight and degree of deacetylation of chitosan. The particles may be tailored to be stable in a variety of environments.

The ionotropic gelation method is commonly used to prepare chitosan particles. This method is based on electrostatic interaction; at physiologic pH, the primary amine groups of chitosan are protonated, and therefore chitosan is positive-charged. The positive charge is used to form particles in solution via cross-linking with polyanions (stabilizer) such as sodium tripolyphosphate (STPP), to efficiently encapsulate the drug via electrostatic interaction, and to promote cellular internalization of drug-containing chitosan particles. Polyanionic stabilizers may function as cross-linkers to form the particles by acting as a negative counterion to the positively charged amine groups on chitosan. This electrostatic interaction forms ionic bonds that support the structure of the particles. Also, the presence of sodium as positive counter-ion may render STPP a more effective cross-linker than other tripolyphosphate (TPP) salts.

Several advantages of this simple and mild method include the use of aqueous solutions, the preparation of particles with a small size, the manipulation of particle size by the variation in pH values, and the possibility of encapsulation of drug during particle formation. Structural changes can be introduced by ionic strength variations, like presence of KCl at low and moderate concentrations emphasize swelling and weakness of chitosan-STPP ionic interactions.

The particles can permeate tissue to deliver encapsulated agents. The particle size is dependent on the pH of the aqueous solution from which they are prepared and the weight ratio of chitosan to STPP, and the size of the particles influences the drug release rates. Other parameters affect the particles including the chitosan:stabilizer (such as STPP) ratio in aqueous solution during the synthesis process, as an increase in the amount of stabilizer leads to a higher degree of chitosan cross-linking and a decrease in the particle dimensions. Accordingly, the size of the particles can be modulated, allowing the use of specific particle size ranges tailored to the tissue for which the particles are chosen.

Salt

The chloride salt of a monovalent cation can be any suitable chloride salt. In some embodiments, the chloride salt of a monovalent cation is NaCl, KCl, LiCl, RbCl, CsCl, NH4Cl, or combinations thereof. In some embodiments, the chloride salt of a monovalent cation is NaCl.

The chloride salt can be present in the polymeric matrix in any suitable amount.

Representative amounts of the chloride salt in the polymeric matrix include from about 10 to about 25% (w/w), or from about 15 to about 25% (w/w), or from about 16 to about 24% (w/w), or from about 17 to about 23% (w/w), or from about 17 to about 22% (w/w), or from about 17 to about 21% (w/w), or from about 17 to about 20% (w/w), or from about 17 to about 19% (w/w). Representative amounts of the chloride salt in the polymeric matrix include about 15% (w/w), or about 16, 17, 18, 19, 20, 21, 22, 23, 24 or about 25% (w/w). In some embodiments, the chloride salt of a monovalent cation is NaCl and is present in the polymeric matrix in an amount of about 18% (w/w) of the polymeric matrix.

Hydration Promoter

The polymeric matrix can include a variety of other components, such as a hydration promoter. Without wishing to be bound to any particular theory, it is believed that the hydration promoter increases moisture absorption by the delivery system. This increase in hydration enables the rapid release and permeation of the microparticles from the matrix. It is also believed that the hydration promoter improves uniformity and durability by acting as a cryoprotectant during the manufacturing process of the delivery system. Again without being bound to any particular theory, it is believed that the hydration promoter acts as a "spacer" between ice crystals and matrix polymer molecules, to ensure a uniform freezing pattern. The resulting structure is more flexible, uniform, and durable than in the absence of the hydration promoter. Representative hydration promoters include, but are not limited to, ethylene glycol, propylene glycol, beta-propylene glycol, glycerol, and combinations thereof.

In some embodiments, the polymeric matrix further comprises a hydration promoter. In some embodiments, the hydration promoter is ethylene glycol, propylene glycol, beta-propylene glycol, glycerol, or combinations thereof. In some embodiments, the hydration promoter is propylene glycol.

The hydration promoter can be present in the polymer matrix in any suitable amount. Representative amounts of the hydration promoter in the polymer matrix include from about 1 to about 50% (w/w), or from about 5 to about 25% (w/w), or from about 5 to about 15% (w/w), or about 5, 6, 7, 8, 9, 10, 11, 12, 13, 14, or about 15% (w/w). In some embodiments, the hydration promoter can be present in an amount of about 7.0% (w/w), or 7.1, 7.2, 7.3, 7.4, 7.5, 7.6, 7.7, 7.8, 7.9, or about 8.0% (w/w). In some embodiments, the propylene glycol is present in the polymeric matrix in an amount of from about 5 to about 25% (w/w). In some embodiments, the propylene glycol is present in an amount of about 7.75% (w/w).

Particle Adhesion Inhibitor

The polymeric matrix can include a variety of other components, such as a particle adhesion inhibitor, for example hydroxypropyl methylcellulose. Without wishing to be bound to any particular theory, it is believed that when the matrix and particles are made of materials bearing polar or ionically charged moieties, such as chitosan, the mobility of the particles suffers. In the instance of chitosan, it is believed that the interactions between acetyl and amine moieties of the polymer cause the particles to adhere to the matrix and inhibit their release.

It has been found that the inclusion of an adhesion inhibitor can mitigate adhesion of the matrix with the particles. Without being bound to any particular theory, it is believed that the adhesion inhibitor acts as a "spacer" between the chitosan of the particles and the chitosan in the body of the matrix, releasing the particles and allowing for improved drug release profiles. In some embodiments, the polymeric matrix further comprises a particle adhesion inhibitor. In some embodiments, the particle adhesion inhibitor comprises hydroxypropylmethylcellulose (HPMC). The molar mass of the HPMC can be from about 1 kDa to about 200,000 kDa, while its viscosity may vary from about 10 cps to 100,000 cps.

The particle adhesion inhibitor can be present in any suitable amount. Representative amounts of the particle adhesion inhibitor include from about 0.1 to about 10% (w/w), or about 1 to about 10% (w/w), or about 2 to about 8% (w/w), or about 3 to about 6% (w/w), or about 3 to about 5% (w/w), or about 3 to about 4% (w/w). Other representative amounts of the particle adhesion inhibitor include, but are not limited to, about 1% (w/w), or about 2, 3.0, 3.1, 3.2, 3.3, 3.4, 3.5, 3.6, 3.7, 3.8, 3.9, 4, 5, 6, 7, 8, 9, or about 19% (w/w). In some embodiments, the hydroxypropylmethylcellulose (HPMC) is present in the polymeric matrix in an amount of from about 0.1 to about 10% (w/w). In some embodiments, the hydroxypropylmethylcellulose (HPMC) is present in the polymeric matrix in an amount of about 3.7% (w/w).

Particle Aggregation Inhibitor

The polymeric matrix can include a variety of other components, such as a particle aggregation inhibitor. Processes for manufacturing the delivery devices include freezing steps during which ice crystals may form within the matrix. Such crystals can force the microparticles into each other, creating particle aggregates where the particles are damaged or destroyed. Again without wishing to be bound to any particular theory, it is believed that aggregation inhibitors exert a cryoprotectant action by forming crystal microstructures which prevent aggregation of the particles. In some embodiments, the polymeric matrix further comprises a particle aggregation inhibitor.

The particle aggregation inhibitor can be present in any suitable amount. Representative amounts of the particle aggregation inhibitor include, but are not limited to, from about 0.1 to about 50% (w/w), or from about 1 to about 30% (w/w), or from about 10 to about 30% (w/w), or from about 20 to about 30% (w/w), or from about 20 to about 25% (w/w), or from about 21 to about 23% (w/w). The particle aggregation inhibitor can also be present in an amount of about 1, 5, 10, 15, 20, 21, 22, 23, 24, 25, 26, 27, 28, 29, or about 30% (w/w). In some embodiments, the particle aggregation inhibitor is present in an amount of from about 0.1 to about 30% (w/w). In some embodiments, the particle aggregation inhibitor is present in an amount of from about 20 to about 25% (w/w). In some embodiments, the particle aggregation inhibitor is present in an amount of about 22% (w/w). In some embodiments, the particle aggregation inhibitor is present in an amount of about 22.25% (w/w).

The particle aggregation inhibitor can include carbohydrates such as, but not limited to, monosaccharides, disaccharides, sugar alcohols, chlorinated monosaccharides, chlorinated disaccharides, and combinations thereof. In some embodiments, the particle aggregation inhibitor is a monosaccharide, disaccharide, sugar alcohol, chlorinated monosaccharide, chlorinated disaccharide, or combinations thereof. Representative monosaccharides include glucose, fructose and galactose, among others. Representative disaccharides include sucrose and lactose. Chlorinated monosaccharides include monosaccharides substituted by at least one chlorine atom. Chlorinated disaccharides include disaccharides substituted by at least one chlorine atom, including, but not limited to, sucralose.

In some embodiments, the particle aggregation inhibitor is sucralose. In some embodiments, the sucralose is present in the polymeric matrix in an amount of from about 0.1 to about 30% (w/w). In some embodiments, the sucralose is present in the polymeric matrix in an amount of about 22.25% (w/w).

Free Therapeutic Agent

It has also been found that when the matrix includes a free quantity of the therapeutic agent, embedded directly in the matrix and not otherwise coated with chitosan in the particles, the device is therapeutically more effective than comparable matrices which include either only a free quantity of the therapeutic agent or only therapeutic agent coated with chitosan. In representative embodiments, the free quantity of the therapeutic agent constitutes between 20-80% of the total quantity of therapeutic agent in the delivery system.

In some embodiments, the polymeric matrix further comprises a free amount of the therapeutic agent in an amount of from about 20 to about 80% of the total amount of the therapeutic agent in the system.

Microparticles

In some embodiments, improved pure chitosan microparticles are provided. Traditional chitosan particles are manufactured with salts of chitosan characterized by a high degree of deacetylation and bearing electrically charged moieties, for example chitosan chloride and chitosan glutamate. It has been found that better results are provided if the particles are made from pure chitosan, a material characterized by not being a salt, that is, with its amine groups unprotonated, and having a degree of deacetylation of at least 70%. In particular, the particles are characterized by larger diameters than traditional particles. In some embodiments, the average diameter of the pure chitosan particles may range from about 200 to about 2000 nanometers. In some embodiments, the average diameter ranges from about 500 to about 2000 nanometers, and in additional embodiments from 500 to 1000 nm.

In some embodiments, the microparticles are embedded within the matrix so as to be directly surrounded by, and in contact with, the polymeric matrix. The microparticles can be present in the system in any suitable amount, such as from 1 to 75% (w/w), or from 10 to 75%, or from 25 to 75%, or from 35 to 65%, or from 45 to 65%, or from 50 to 60%. The microparticles can be present in the system in any suitable amount, such as about 1% (w/w), or about 5, 10, 15, 20, 25, 30, 35, 40, 45, 50, 55, 60, 65, 70, or about 75% (w/w) of the system. In some embodiments, the microparticles are present in the polymeric matrix in an amount of from about 10 to about 40% (w/w). In some embodiments, the microparticles are present in the polymeric matrix in an amount of from about 45 to about 65% (w/w). In some embodiments, the microparticles are present in the polymeric matrix in an amount of about 55% (w/w).

Therapeutic Agents

Any therapeutic, prophylactic, diagnostic or nutraceutical agent which is capable of encapsulation and release may be used. Representative agents include biologics, peptides, nucleotides, anti-infectives, antibiotics, antifungals, antivirals, anti-inflammatories, immunomodulators, vaccines, and combinations thereof. Other agents include calcium mobilizers such as nicotinic acid adenine dinucleotide phosphate and peptides such as glucagon-like peptide-2. Nicotinic acid adenine dinucleotide phosphate and other calcium mobilizers have been shown to promote ISC proliferation and intestinal epithelium regeneration. Glucagon-like peptide-2 and its analogs have also been shown to promote ISC proliferation and intestinal epithelium regeneration. The efficacy of nicotinic acid adenine dinucleotide phosphate and glucagon-like peptide-2 have been shown to be hindered by a lack of proper targeting and delivery within the GI tract. The particle-based system provided herein remedies such drawbacks.

Platin Antineoplastic Agents

The particles can also include any suitable antineoplastic agent. In some embodiments, the therapeutic agent comprises an antineoplastic agent. Representative antineoplastic agents include platinum antineoplastic agent, 5-fluorouracil (5-FU), and others. In some embodiments, the platinum antineoplastic agent comprises cisplatin, carboplatin, oxaliplatin, nedaplatin, triplatin tetranitrate, phenanthriplatin, picoplatin, satraplatin, or combinations thereof. In some embodiments, the therapeutic agent includes carboplatin, cisplatin, oxaliplatin, malonato platinum, ormaplatin, 5-fluorouracil, NAADP, allantoin, insulin, FITC, or rapamycin. In some embodiments, the therapeutic agent comprises cisplatin. In some embodiments, the therapeutic agent comprises carboplatin. In some embodiments, the therapeutic agent comprises allantoin.

The antineoplastic agent can be present in any suitable amount. Representative amounts of the antineoplastic agent include, but are not limited to, from about 0.1 to about 30% (w/w), or from about 1 to about 30% (w/), or from about 10 to about 30% (w/w), or from about 20 to about 30% (w/w), or from about 20 to about 25% (w/w), or from about 21 to about 23% (w/w). The antineoplastic agent can also be present in an amount of about 1, 5, 10, 15, 20, 21, 22, 22.1, 22.2, 22.3, 22.4, 22.5, 22.6, 22.7, 22.8, 22.9, 23, 24, 25, 26, 27, 28, 29, or about 30% (w/w). In some embodiments, the platinum antineoplastic agent is present in an amount of from about 0.1 to about 30% (w/w). In some embodiments, the platinum antineoplastic agent is present in an amount of from about 20 to about 25% (w/w). In some embodiments, the platinum antineoplastic agent is present in an amount of about 22% (w/w). In some embodiments, the platinum antineoplastic agent is present in an amount of about 22.5% (w/w).

In some embodiments, the system comprises from about 1 to about 50% (w/w) of cisplatin. In some embodiments, the system comprises about 22.5% (w/w) of cisplatin.

The patch makes use of well-known chemotherapeutics in some embodiments as well as commercially available excipients, additionally minimizing the costs associated with its manufacture. The simple manufacturing process, relatively low overall costs, and easy method of administration serve as improvements over all existing intraoperative treatment methods, and will promote a widespread uptake and utilization of the present invention.

In some embodiments, the patch contains a combination of two or more chemotherapeutics to be delivered to a surgical cavity within the abdomen, pelvis and/or intraperitoneal region, where each of the chemotherapeutics is present at some ratio of freeform chemotherapeutic to particle-encapsulated chemotherapeutic. In some embodiments where two or more chemotherapeutics are included, one chemotherapeutic may be encapsulated within particles while the other remains freeform. For example, if cisplatin and oxaliplatin are desired chemotherapeutics for inclusion within the patch, one such chemotherapeutic (cisplatin) may be included in particle form while oxaliplatin may be included in freeform.

In some embodiments where two or more chemotherapeutics are included, one chemotherapeutic may be encapsulated within particles while the other exists both in freeform and within particles. For example, if cisplatin and oxaliplatin are desired chemotherapeutics for inclusion within the patch, one such chemotherapeutic (cisplatin) may be included in particle form while oxaliplatin may be included both in freeform and encapsulated within particles. In additional embodiments where two or more chemotherapeutics are included, two or more of the chemotherapeutics may be included both within particles and both in freeform. For example, if cisplatin and oxaliplatin are desired chemotherapeutics for inclusion within the patch, both cisplatin and oxaliplatin may exist encapsulated both within particles and additionally in freeform at a desired ratio within the final patch product.

In some embodiments, at least one agent included within the patch is an anti-infective agent, which may be included in freeform, encapsulated within particles, or a combination thereof. In some embodiments, at least one agent included within the patch is an anti-bacterial or anti-viral agent, which may be included in freeform, encapsulated within particles, or a combination thereof. In some embodiments, the majority of particles range in diameter from 60 nanometers to 2 microns. In some embodiments, the particles have an average diameter between 100 nm and 1000 nm. In some embodiments, the particles have an average diameter of 200-500 nm or of 100 to 400 nm.

Sodium Tripolyphosphate

Without wishing to be bound to any particular theory, it is believed that the sodium tripolyphosphate (STPP) functions as a cross-linker to form the particles by acting as a negative counter-ion to the positively charged amine groups on chitosan. This electrostatic interaction forms ionic bonds that support the structure of the particles. Also without wishing to be bound to any particular theory, it is believed that the presence of sodium as positive counterion renders STPP a more effective crosslinker than other TPP salts.

In some embodiments, the microparticles further comprise sodium tripolyphosphate.

Representative amounts of the sodium tripolyphosphate include, but are not limited to, from about 0.1 to about 10% (w/w), or from about 2 to 8% (w/w), or from about 2 to about 5% (w/w), or about 2 to about 4% (w/w), or about 1, 2, 3, 4, 5, 6, 7, 8, 9, or about 10% (w/w). In some embodiments, the system comprises from about 0.1 to about 10% (w/w) of sodium tripolyphosphate. In some embodiments, the system comprises about 3.0% (w/w) of sodium tripolyphosphate.

System

In some embodiments, the polymeric matrix comprises: chitosan in an amount of from about 20 to about 30% (w/w); cisplatin in an amount of from about 20 to about 30% (w/w); NaCl in an amount of from about 10 to about 18% (w/w); propylene glycol in an amount of from about 5 to about 25% (w/w); hydroxypropylmethylcellulose (HPMC) in an amount of from about 0.1 to about 10% (w/w); sucralose in an amount of from about 0.1 to about 30% (w/w); and the microparticles in an amount of from about 10 to about 40% (w/w).

In some embodiments, the polymeric matrix comprises: chitosan in an amount of about 22.5% (w/w); cisplatin in an amount of about 22.5% (w/w); NaCl in an amount of about 18% (w/w) of the polymeric matrix; propylene glycol in an amount of about 7.75% (w/w); hydroxypropylmethylcellulose (HPMC) in an amount of about 3.7% (w/w); sucralose in an amount of about 22.25% (w/w); the microparticles in an amount of about 55% (w/w).

Backing Layer

The system can also include a backing layer. Representative backing layers include a water-permeable backing layer. The backing layer prevents significant loss of payload components in the device from diffusion through the second surface, and optionally protects the device from an environment. The backing layer may include a material selected from the group consisting of a polyacrylate adhesive, a non-woven polyester fabric backing, or combinations thereof.

In some embodiments, the polymer matrix has first and second opposed surfaces, and wherein the system further comprises a water-permeable backing layer applied to the first surface of the polymeric matrix.

Adhesive Layer

In some embodiments, the second surface comprises a polyacrylate adhesive, a non-woven polyester fabric, or combinations thereof.

Method of Manufacturing

The present invention also provides a method for manufacturing a delivery device for delivering a therapeutic agent to a tissue, the method comprising: forming a first mixture with a plurality of particles, the particles containing a therapeutic agent and having a coating around the therapeutic agent, the coating including chitosan; adding chitosan, a hydration promoter, a particle adhesion inhibitor, a particle aggregation inhibitor or combinations thereof to the first mixture, to form a second mixture; freezing the second mixture in a bath containing an aqueous alcoholic solution at a temperature above the freezing temperature of the aqueous alcoholic solution and at most −40° C., to form a frozen layer precursor; drying the frozen layer precursor, to form a porous patch with particles embedded within a polymeric matrix of the patch; and sterilizing the patch.

In some embodiments, a method of manufacturing of a multi-layered device and a formulation created according to such method are provided. The method includes the freezing and freeze drying of polymeric solutions containing a therapeutic agent.

Precursor mixtures are first created, then subjected to freezing or freeze drying. The device may feature multiple layers, and the precursor mixture to each layer may be separately made. All layers may each contain an independently chosen agent to be delivered, and at least one layer contains microparticles which further encapsulate at least one of the agents. The microparticles may be synthesized, for instance, according to the ionotropic gelation method, where no modification of the agent takes place. Microparticles are designed to range from 200 to 2000 nanometers, from 500 to 2000 nanometers, or from 500 to 1000 nm in average diameter. Agents such as a permeation enhancer, taste masking elements and agents for the formation of body structure may be added. These agents may include propylene glycol, hydroxypropylmethylcellulose, chitosan, sweeteners, peppermint or other flavorings, among many others. Solutions containing agents but no microparticles may also contain these and other agents.

Once ready, the precursor mixtures are subjected to freezing. It is preferable that the layers of the device be first frozen in a freezing bath of an aqueous alcohol at a temperature of at most −40° C., for example in a bath of aqueous ethanol and dry ice. This method has been found to result in a device which is able to release nearly all of its agent content and permeate deeply into the desired mucosal depths. Without wishing to be bound to any particular theory, the product device is more effective as compared to other methods of freezing. When the precursor mixture was frozen via liquid nitrogen, placement in a freezer at −80° C., or standalone dry ice, some of the microparticles burst and the polymer in the matrix of the device became more rigid, resulting in a low percentage of agent release and a compromised therapeutic efficacy. The bath can include dry ice completely covered by a solution of at least 90 wt % ethanol in water. The precursor mixture of the first layer of the device (in liquid form) is poured into a mold, for example a silicone molding and is submerged approximately ⅔ to ¾ in the bath of ethanol and dry ice, to form a frozen layer. Preferably, thirty minutes should be allowed to achieve complete freezing.

After freezing the initial layer, a second layer may be added by one of two methods. In the first method, the precursor mixture of the second layer is poured in liquid form on top of the frozen first layer while the first layer remains in the ethanol/dry ice bath. The resulting frozen bottom layer and liquid top layer are then submerged more deeply until a ⅔ to ¾ overall submersion ratio is met. Another 30 minutes are allowed for complete freezing of the second layer. Subsequent layers in excess of two may be added by the same process.

In the second method, each layer is separately and concurrently frozen in its individual mold within the freezing bath. After thirty minutes are allowed to ensure complete freezing of each layer, a coating of an solution of one or more salts, for example 0.12% saline, is brushed onto the first, initial layer. Within about a minute of the application of the coating, the second layer is applied onto the first and a pressure of about 0.25 kg is applied. This results in a combined solid. Subsequent layers in excess of the second layer can be applied by the same method.

After all the desired layers have been added, the device is moved into a lyophilization chamber for about one to three days, depending on the number of devices loaded into the chamber. After the lyophilization removes all liquids, the multi-layer device is ready for use.

In some embodiments, a multi-layered device may be used for the delivery of multiple agents over a concurrent period of time. For example, if use for the treatment and pain mitigation of mucositis is desired, one layer may include a pain mitigator, and one layer may include an agent for the treatment of mucositis.

In some embodiments, a multi-layered device may be used for the delivery of multiple agents over a prolonged period of time. If the example of mucositis is again used, multiple layers may include a pain mitigator in free form, a pain mitigator encapsulated within microparticles and an agent for the treatment of mucositis encapsulated within microparticles. The initial freeform layer is able to provide immediate pain relief, and the subsequent particle-encapsulated layers are capable of delivering microparticles beneath the tissue, where they further release their agents over a period of days, providing longer-term pain relief and treatment.

Once the patch is prepared, the patch can be subjected to a sterilization process that ensures that the final product meets the sterility requirements of surgery applications while not appreciably degrading the components or performance of the patch. In particular, care should be taken that the sterilizing process does not significantly affect the structure and efficacy of the therapeutic agent contained in the patch. Gamma ray irradiation, which uses radiation emitted from radioactive isotopes such as Cobalt 60 to kill microorganisms, has been found to effectively sterilize patches while leaving chemotherapeutic agents essentially unaffected.

In some embodiments, the present invention provides a method of preparing the system of the present invention, comprising forming a first mixture comprising water, chitosan, a chloride salt, a hydration promoter, a particle adhesion inhibitor, and a particle aggregation inhibitor, to prepare a matrix mixture; forming a second mixture comprising the matrix mixture, a first platinum antineoplastic agent, and chitosan microparticles comprising a second platinum antineoplastic agent; removing the water from the second mixture, to prepare a dried mixture; and applying the dried mixture to a backing layer, thereby preparing the system.

In some embodiments, the method of preparing the system of the present invention includes forming the first mixture comprising water, chitosan, a chloride salt, propylene glycol, hydroxypropyl methyl cellulose, and sucralose, to prepare the matrix mixture; forming a second mixture comprising the matrix mixture, cisplatin, and chitosan microparticles comprising chitosan, cisplatin and sodium tripolyphosphate; removing the water from the second mixture, to prepare the dried mixture; and applying the dried mixture to the backing layer, thereby preparing the system of the present invention.

In some embodiments, the present invention provides a method of preparing a system of the present invention, comprising:

- forming a first mixture comprising water, chitosan, and acetic acid;
- forming a second mixture comprising a chloride salt, a therapeutic agent, and sodium tripolyphosphate;
- forming a third mixture comprising the first mixture and the second mixture, thereby forming microparticles;
- forming a fourth mixture comprising water, chitosan, acetic acid, a hydration promoter, and a particle adhesion inhibitor;
- forming a fifth mixture comprising the fourth mixture, a particle aggregation inhibitor, and the microparticles, to form the polymer matrix;
- removing the water from the polymer matrix, to prepare a dried mixture; and
- applying the dried mixture to a backing layer, thereby preparing a system of the present invention.

In some embodiments, the method comprises:

- forming the first mixture comprising water, chitosan, and acetic acid;
- forming the second mixture comprising sodium chloride, cisplatin, and sodium tripolyphosphate;
- forming the third mixture comprising the first mixture and the second mixture, thereby forming the microparticles;
- forming the fourth mixture comprising water, chitosan, acetic acid, propylene glycol, and hydroxypropyl methyl cellulose;
- forming the fifth mixture comprising the fourth mixture, sucralose, and the microparticles, to form the polymer matrix;
- removing the water from the polymer matrix, to prepare the dried mixture; and
- applying the dried mixture to the backing layer, thereby preparing the system.

IV. Localized Delivery of Agents

In some embodiments, one or more of the above improvements may be applied to a multi-layered agent delivery device. The multi-layered device is capable of delivering the same or multiple agents in phases over a period of time or delivering multiple agents concurrently via modulation of the makeup of each layer. The device and a method for manufacturing such device have been developed to address the unmet need of delivering agents in a multitude of forms locally to mucosal tissue. The multiple layers within this platform may be used for varying purposes.

Traditional drug delivery to a mucosa consists of an initial bolus dose of agent followed by a steady reduction in exposure over time. This platform is able to mitigate this tendency via its multiple layers and the inclusion of microparticle within at least one layer. The material forming the structure of each layer can be optionally chosen to degrade slowly, and the same agent (such as cisplatin for the local treatment of a cancerous tumor) may be chosen for inclusion within each of the multiple layers.

In some embodiments, the device therefore can be designed to release cisplatin locally in multiple phases, providing significantly longer treatment without the side effects, multiple doses required or dose limiting hindrances associated with cisplatin that is parenterally administered. The inclusion of microparticles within this device further assists in the device's ability to provide a sustained local dosage. The microparticles included within this device are released once it is applied, permeate the mucosal tissue, and remain local within the tissue beneath which the device was applied. These microparticles then degrade over a period of time, further providing a sustained, longer dosage of agents. When different agents are included within each layer, additional objectives are able to be achieved. For example, if the device is applied for the treatment of a recently acquired open wound, a pain mitigator and anti-infective agent can each be included within a layer.

When applied within the oral cavity, the device is placed directly onto affected oral tissue within the mouth and releases agents for controlled and targeted treatment of oral diseases. Agents which may be included in free form (such as a pain mitigator in the first layer) may be designed to have an immediate effect to the underlying tissue, whereas agents encapsulated within microparticles (such as a chemotherapeutic pharmaceutical) may be included within a second or subsequent layer. The microparticles are then able to act independent of the first agent, permeate the underlying tissue, and provide a sustained, longer term delivery of agent to the tissue. This device overcomes deficiencies of other prior art by offering the ability to modulate the duration and treatment order parameters to provide multiple stages and durations of treatment.

In some embodiments, the present invention provides a method of administering a therapeutic agent to a subject in need thereof, comprising applying a system of the present invention to the subject such that at least 50% of a therapeutic agent of the system is released from the system in less than 30 minutes.

The system can be applied to any suitable tissue of the subject. Representative tissues include, but are not limited to, skin, mucosal membrane, oral cavity, vagina, and rectum. In some embodiments, the system is applied to a mucosal membrane of the subject. In some embodiments, the system is applied to an oral cavity of the subject. In some embodiments, the system is applied to the skin of the subject.

The therapeutic agent can be administered to the subject at any suitable rate. For example, at least 50% of the therapeutic agent of the system is release from the system in less than 60 minutes, or at least 75% of the therapeutic agent of the system is release from the system in less than 60 minutes, or at least 90% of the therapeutic agent of the system is release from the system in less than 60 minutes, or at least 50% of the therapeutic agent of the system is release from the system in less than 45 minutes, or at least 50% of the therapeutic agent of the system is release from the system in less than 30 minutes, or at least 50% of the therapeutic agent of the system is release from the system in less than 15 minutes.

In some embodiments, at least 75% of the therapeutic agent of the system is release from the system in less than 45 minutes, or at least 75% of the therapeutic agent of the system is release from the system in less than 30 minutes, or at least 75% of the therapeutic agent of the system is release from the system in less than 15 minutes. In some embodiments, at least 75% of the therapeutic agent of the system is released from the system in less than 30 minutes.

In some embodiments, at least 90% of the therapeutic agent of the system is release from the system in less than 45 minutes, or at least 90% of the therapeutic agent of the system is release from the system in less than 30 minutes, or at least 90% of the therapeutic agent of the system is release from the system in less than 15 minutes. In some embodiments, at least 90% of the therapeutic agent of the system is released from the system in less than 30 minutes. In some embodiments, at least 90% of the therapeutic agent of the system is released from the system in less than 15 minutes.

V. Kits

Also provided is a kit including the device and a permeation enhancing agent. Example permeation enhancing agents are selected from the group consisting of dodecyl-2 (N,N-dimethylamino) propionate, bile salts, surfactants, fatty acids, glycerides, polyacrylic acid derivatives, chelating agents, nitric oxide donors, salicylates, chitosan, zona occludens toxins, sodium cholate, sodium deoxycholate, sodium glycodeoxycholate, sodium taurocholate, sodium glycocholate, N-lauryl-b-maltopyranoside, and combinations thereof. Example surfactants include oleic acid, sodium dodecyl sulfate, sodium lauryl sulfate, Polysorbate 80, lauryl esters, and combinations thereof.

In some embodiments, at least one patch is included as a component of a kit for the treatment of abdominal, pelvic and/or intraperitoneal diseases which are accessible via surgery. This kit may include materials that are required for proper administration of the patch as well as proper and safe disposal of the patch after application and cleaning of the treated area. For example, FOLFOX (5-FU, leucovorin, and oxaliplatin) or CapeOx (capecitabine and oxaliplatin) regimens are known, common agents for the treatment of traditional colon cancer. These chemotherapeutics can be utilized in a safe manner to topically treat colon tumors which may have metastasized within the abdomen/pelvis. However, extensive precautions must be taken to ensure that (1) proper handling procedures are followed during treatment, (2) time to prepare and administer the patch is reduced to minimize the time within which the patient's abdomen/pelvis remain exposed, and (3) ensure that contact is minimized between these agents and both the patient and personnel applying the patch. Items that may then be included in the kit for the purpose of safety can include forceps or other tools for the placement of the patch, disposable packaging for any remaining portion of the patch after application and other safety components.

The release of agent(s) from the device is activated in part by exposure to moisture. Therefore, a moisturizing solution such as saline may be provided with the device to be used during the application process. Further, permeation enhancers in powder or solution form may be included to be externally applied to the mucosa prior to application of the device. The permeation enhancer may optionally be included in the form of a powder which requires reconstitution. The powdered form may be included to maintain stability of the permeation enhancer. When included in this form, the kit may optionally include additional materials among which at least one glass vial (5 mL to 20 mL in size) containing sterile water to be used for reconstitution. The kit may additionally include syringes (such as 3 mL Luer-lock syringes) and aspirating needles (such as 18 G needles) to be used for reconstitution of the permeation enhancer.

In addition, when the device is used for certain indications (such as oral indications), care must be taken to ensure that the product is safely applied and removed to prevent choking or swallowing. The kit disclosed herein addresses these concerns by including all materials necessary to ensure the safe application device. Example kits include at least one pair of forceps (either multi-use metal forceps or single use disposable plastic forceps) or other similar instrument used to position and place the device to prevent exposure of agents to people or exposure of the device to the throat.

Disposable packaging can also be included within the kit to ensure the safe disposal and non-contamination of the treatment process by isolating the materials used during treatment. This packaging may include a hazardous waste package used when toxic drugs such as those used to treat oral cancer or melanoma are administered, or biohazard packaging. Additionally, empty scintillation vials may be included to collect the used device post-treatment for purposes such as residual-agent analysis.

VI. Methods of Treating Skin Diseases

In some embodiments, the present invention provides a method of treating a skin disease of a subject in need thereof, comprising applying a system of the present invention to the skin of the subject such that a therapeutically effective amount of a therapeutic agent of the system is released from the system and administered to the skin of the subject, thereby treating the skin disease.

The therapeutic agent can be released from the system of the present invention at any suitable rate, as described above. In some embodiments, at least 50% of the therapeutic agent is released from the system in less than 30 minutes.

The methods of the present invention can be used to treat a variety of skin diseases or skin disorders. Representative skin diseases include, but are not limited to, disease such as skin aging, skin efflorescences including pressure sores, decubital ulcers, irritated, sensitive and dysaesthetic skin, erythema, rash, skin edema, psoriasis, eczema, lichen, bacterial, viral, fungal and parasites induced skin infections including furuncle, abscess, phlegmon, erysipelas, folliculitis and impetigo, lice, scabies and herpes simplex, acne, exanthema, dermatitis including atopic dermatitis, allergic contact dermatitis (Scholzen, T. E.; Luger, T. A. Exp Dermatol. 2004; 13 Suppl 4:22-6) neurodermatitis, radiation damage, sunburn, pruritus, itching, urticaria (EP0622361; Frigas, E.; Park, M. Immunol. Allergy Clin. North Am. 2006, 26, 739-51; Luquin, E.; Kaplan, A. P.; Ferrer, M. Clin. Exp. Allergy 2005, 35, 456-60; Kaplan, A. P.; Greaves, M. W. J. Am. Acad. Dermatol. 2005, 53, 373-88; quiz 389-92), psoriasis, mycosis, tissue ulceration, epidermolysis *bullosa*, wounds including abnormal wound healing, burns (Nwariaku, F. E.; Sikes, P. J.; Lightfoot, E.; Mileski, W. J.; Baxter, C. Burns 1996, 22, 324-7; Neely, A. N.; Imwalle, A. R.; Holder, I. A. Burns 1996, 22, 520-3), frostbite, skin inflammation and edema caused by venoms, alopecia, hair squama, corn, wart and panaris.

Other skin diseases include keratinization skin diseases. Representative keratinization skin diseases include, but are not limited to, Darier's disease, Hailey-Hailey disease, erythrodermic autosomal recessive lamellar ichthyosis, nonerythrodermic autosomal recessive lamellar ichthyosis, autosomal dominant lamellar ichthyosis, bullous congenital ichthyosiform erythroderma, palmoplantar keratosis, erythrokeratodermia variabilis, verrucous epidermal nevi, *Pityriasis rubra pilaris*, Netherton syndrome, idiopathic vulgaris, ichthyosis vulgaris, monilethrix, keratosis piliaris, bullous ichthyosiform erythroderma, nonbullous congenital ichthyosis, Sjogren-Larsson syndrome, erythrokeratodermica variabilis, hyperkeratosis lenticularis perstans, eythrokeratodermia figurate variabilis, mutilating keratosis of Vohwinkel, Harlequin ichthyosis and Tay's syndrome (International Patent Application PCT/US2009/031101).

A new terminology for the keratinization skin disorders has been recently introduced (see Akiyama M. et al., J Dermatol Sci. 2018 May; 90(2):105-111, "Autoinflammatory keratinization diseases: An emerging concept encompassing various inflammatory keratinization disorders of the skin").

In some embodiments, the skin disease is skin cancer, inflammatory skin disease, autoimmune skin disease, acne, atopic dermatitis, contact dermatitis, eczema, impetigo, rashes, psoriasis, plaque psoriasis, or Behcet's disease. The inflammatory skin disease can include, but is not limited to, acne, psoriasis, rosacea, eczema, actinic keratosis, ichthyosis, Bowen's disease, keratoacanthoma, *Lichen sclerosus*, hidradenitis suppurativa, *Pityriasis* lichenoid, dermatitis, atopic dermatitis, contact dermatitis, eszematous dermatitis, or seborrheic dermatitis. In some embodiments, the skin disease is basal cell carcinoma, squamous cell carcinoma, or melanoma.

In some embodiments, the skin disease is an inflammatory skin disease. In some embodiments, the inflammatory skin disease or disorder is selected from psoriasis, atopic dermatitis (AD), eczema, actinic keratosis, ichthyosis, *Pemphigus vulgaris*, acne, Grover's disease (transient acantholytic dermatosis), keratoacanthoma, hidradenitis suppurativa, seborrheic keratosis, *Pityriasis* lichenoid, alopecia areata, basal cell carcinoma, Bowen's disease, congenital erythropoietic *porphyria*, contact dermatitis, Darier's disease, dystrophic epidermolysis *bullosa*, pidermolysis *bullosa* simplex, erythropoietic protoporphyria, fungal infections of nails, herpes simplex, hidradenitis suppurativa, ichthyosis, impetigo, keloids, keratosis pilaris, lichen planus, *Lichen sclerosus, Pemphigus vulgaris*, plantar warts (verrucas), *Pityriasis lichenoides*, polymorphic light eruption, pyoderma gangrenosum, rosacea, shingles, squamous cell carcinoma, Sweet's syndrome, and vitiligo. In some embodiments, the inflammatory skin disease is caused by microbial infection-induced dermatitis, solar dermatitis, atopic dermatitis, or allergic contact dermatitis. In some embodiments, the inflammatory skin disease or disorder is psoriasis. In some embodiments, the inflammatory skin disease or disorder is atopic dermatitis (AD).

In some embodiments, the skin disease is an autoimmune skin disease. In some embodiments, the autoimmune skin disease is lupus, psoriasis, atopic dermatitis, alopecia areata, or Behcet's disease.

VII. Methods of Treating Cancer

Oral mucositis is also a significant disease due in part to the fact that it can occur in the mouth when systemic chemotherapy is given for any reason, not only oral cancer. In some embodiments, the treatment device within the disclosed kit may include agents which treat or relieve pain, or otherwise address oral mucositis. Unlike existing treatments for mucositis, the current kit includes a device which contains agent-encapsulated microparticles within it. In a manner similar to its effect treating oral cancer, the microparticles released from the device are mucoadhesive so that they remain local to the site of the mucositis. Since the particles are nanoscale, they are able to permeate the tissue and release the encapsulated agent deeper within the affected area than other current treatments, and without broader exposure of the agent. Administration via this kit is able to offer a much more effective delivery of agents to areas affected by mucositis.

In some embodiments, the described kit is also used to deliver agents for the treatment of precancerous/premalignant oral lesions. Precancerous/Premalignant lesions are often left untreated when detected due to a lack of ideal treatment options. A diagnosis is often coupled with monitoring for malignancy rather than early treatment because chemotherapy or surgery can be considered too extreme for early lesions. It is also difficult to differentiate between precancerous/premalignant lesions and other non-malignant lesions. For this reason, there often exists an unwillingness to administer damaging systemic chemotherapy for a potentially non-life threatening issue. To address these conditions, the present kit can be used to administer lower dosages of chemotherapeutics or other agents to these lesions. Treatment would be able to be administered on a much larger scale due to the higher efficacy achieved with such a small dosage and the significantly higher safety. For these reasons, the present kit is viewed as a significant improvement and viable alternative to current treatment methods. Furthermore, the inclusion of the treatment device within a kit is also viewed as a significant improvement over U.S. application number US 2014/0234212 in which the treatment device alone is disclosed due to the safety and efficacy reasons described above.

In some embodiments, the kit includes a mucoadhesive drug delivery device containing active agent-encapsulating microparticles and items useful for the successful administration and disposal of the device, such as: an oral permeation enhancer either incorporated within the delivery device or provided within the kit alongside it, and an oral rinse used to cleanse the mouth prior to or following treatment.

In some embodiments, the present invention provides a method of treating a mucosal cancer, comprising applying the system of the present invention to the mucosal cancer of a subject in need thereof, thereby treating the mucosal cancer. In some embodiments, the mucosal cancer is an oral cancer. In some embodiments, the system of the present invention is applied to a tumor in an oral cavity of the subject in need thereof.

VIII. Method of Gastrointestinal Delivery of Agents

In some embodiments, a disclosed particle-based agent delivery system has been developed for the treatment of gastrointestinal diseases and conditions. The delivery device disclosed herein is in part effective because of its ability to adhere to the intestinal mucosa.

The properties of mucus itself must first be understood to properly develop a delivery system. Mucus is a viscoelastic gel layer that protects tissues that would otherwise be exposed to the external environment. Mucus is composed primarily of crosslinked and entangled mucin fibers secreted by goblet cells and submucosal glands. Mucins are large molecules, typically 0.5-40 MDa in size, and coated with a complex and highly diverse array of proteoglycans. Mucus pH can vary greatly depending on the mucosal surface, with highly acidic environments capable of aggregating mucin fibers and greatly increasing the mucus viscoelasticity. In the human GI tract, the mucus layer is thickest in the stomach and the colon. Gastric mucus is exposed to a wide range of pH: a large pH gradient exists within the same mucus cross-section, with pH rising from the luminal pH of 1-2 to 7 at the epithelial surface.

Accordingly, provided herein is a gastrointestinal drug delivery system capable of modulating the release of agents depending on the environmental pH, thereby making possible the specific targeting of drugs within the gastrointestinal tract. Described herein are efforts to target drug delivery to the gastrointestinal tract through the design of a mucoadhesive delivery system which releases its payload only within the pH environment of the gastrointestinal (GI) tract, and, more specifically, to specific regions within the GI tract. Because of the mucous lining of the GI tract, attraction to the mucosa and mucoadhesivity are important elements of this device.

In the case of orally administered agents for gastrointestinal delivery, survival through digestive regions of extreme pH values is necessary. In the human stomach, the volume of gastric fluid ranges from 20 to 100 ml with a pH of 1.5-3.5. Gastric fluid consists of hydrochloric acid, potassium chloride and sodium chloride. Fluid secretion takes place over several stages. Hydrogen and chloride ions are secreted and mixed in the canaliculi. The lumen of the oxyntic gland secretes the gastric acid which reaches the stomach lumen. Secretion of the chloride and sodium ions creates a negative potential of approximately −35 to −65 mV, which allows for diffusion of the potassium and sodium ions from the cytoplasm.

Carbonic anhydrase forms carbonic acid by catalyzing reactions between water and carbon dioxide. This allows for the dissociation into hydrogen and bicarbonate ions. The hydrogen ions then move from the cell. Sodium ions are reabsorbed. In the canaliculus, hydrogen and chloride ions mix and are secreted into the lumen of the oxyntic gland.

Gastric acid production is separated into three phases. The first of these is the cephalic phase, where approximately 30% of gastric acid production is stimulated by the smell, taste, or expectation of food as signaled by the brain. About 50% of gastric acid is produced during the gastric phase, where stimulation of production occurs by food presence in the stomach and release of amino acids from consumed materials. The intestinal phase represents the last phase of acid production, where the remaining 20% of acid is produced when chyme (semifluid of partially digested food) enters the small intestine. If agents targeted to the gastrointestinal mucosa are to be delivered orally, the delivery system must remain intact and stable through the gastric acid of the stomach. Through the development of a system which is able to remain stable in this environment as well as multiple pH conditions, oral administration for delivery of an agent into and within the gastrointestinal mucosa is made possible. As opposed to traditional products with an enteric coating, this system is both able to withstand a multitude of pH levels as well as contain a combination of particles which are able to release in desired pH conditions.

In order for orally administered alternatives to enteric capsules to be efficacious in the treatment of gastrointestinal diseases, such alternatives should possess the capability of remaining stable throughout the entire described acidic and dynamic stomach digestion process. Likewise, since many GI diseases may encompass multiple regions of the GI tract that span multiple pH ranges, the development of a delivery system that is able to withstand and release over various pH changes is advantageous. An efficacious alternative should also be characterized by the ability of becoming attracted by means of mucoadhesivity to the intestinal mucosa lining and releasing upon contact or at a designated time thereafter. Thus, provided herein is a therapeutic, diagnostic and/or prophylactic delivery device for local and systemic administration and delivery into the gastrointestinal stem cells and/or systemically beyond, which is able to become attracted/attach to and penetrate through the intestinal mucosa as well as remain stable in acidic stomach conditions. The devices described herein are able to provide an extended or delayed release, programmable release, and site specific release into and within gastrointestinal locations.

In many instances, oral administration is not possible if the patient is unable to swallow a capsule or tablet. This can occur with young children where compliance is low or among the elderly where pain exists or there is otherwise an inability to take oral medication. People with feeding or nasogastric tubes are other examples of these cases. In some embodiments, the present invention provides a method of oral delivery of agents to patients who otherwise would be unable to be administered oral agents. This is in part accomplished through the optional use of liquid and gelatin forms of oral administration for those who cannot swallow solid tablets or capsules, as well as through nasal administration or consumption through a nasogastric or feeding tube. Compared to traditional administration techniques, the delivery system provides for the successful delivery through theses avenues. Particles may be provided in a variety of forms and tailored to specific needs.

The gastrointestinal delivery system also provides a therapeutic, diagnostic and/or prophylactic delivery device that is effective in the presence or potential presence of gastrointestinal fluids, in contrast to the traditional washout problems described above associated with such fluids. Also provided is a route for administering a therapeutic, diagnostic and/or prophylactic agent to one or multiple specific regions of the intestinal epithelia through the design of a system containing one or more sets of particles able to withstand and release through a multitude of pH ranges.

For these and other purposes, the gastrointestinal delivery system disclosed herein may serve as a device for specific, targeted delivery within the gastrointestinal tract to the gastrointestinal mucosa. In some embodiments, the delivery device adheres to the gastrointestinal mucosal tissue, is able to withstand the low pH, acidic environment of the stomach and contains pH-targeted, mucoadhesive particles in which one or more agents are encapsulated. The device may also include permeation enhancers sufficient to facilitate agent permeation through the mucosal layer of the gastrointestinal tract.

One of the unique properties of this platform is that the release and targeting attributes can be controlled based on desired parameters. The particles may be controlled to remain stable within a desired pH level and release in another desired pH level. This ability may be used to create a combination of targeted particles which can remain stable through any component of the GI tract regardless of pH exposure, including the stomach, esophagus, and components of the intestines.

In addition to stability, the timing of release of the agents encapsulated within the particles may be controlled. The purpose of this feature is to further target the delivery to locations within the GI tract. For example, if it is known that under normal digestion conditions, a known amount time is known to intercur between oral consumption and delivery to the desired delivery, the particles within the delivery system may be further designed to release their agent payload at such amount of time after oral contact is made with the delivery system. A formula has been developed by which the release time may be determined. The parameters and formula are identified below:

| |
|---|
| Degree of Deacetylation (DA) |
| Molecular Weight (MW) combinations, |
| Time (T) |
| Amount of exposure to humidity, water content (WC) |
| Solution pH (SpH) at the synthesis stage |
| Degree of Viscosity (DV) |
| Synthesis technique (K is a constant) such as freezing method of the particles |
| Formula: |
| ** Degree of release (DR) = a (DA) + b (MW) + c (SpH) + d(T) + e(WC) + f(DV) + k |

** It has been discovered that the use of sodium nitrite allows for further modulation of the degree of deacetylation and molecular weight of chitosan.

The pH modulation and configurable release timing increases the efficacy of the delivery system and shows how innovative it is compared to traditional systems. Without wishing to be bound to any particular theory, it is believed that such superior properties are the product of previously unknown effects of the degree of deacetylation and molecular weight of the chitosan. Using the varying pH levels of the GI tract and the relationship between pH and location, delivery can be targeted. For example, particles can be programmed to release at pH levels of only between 5.8 and 6.2, thereby making possible the specific targeting to the duodenum.

Targeting release to multiple locations can be achieved by the inclusion of a blended mix of customized particles within the delivery system. This allows for targeting to an array of desired locations if a disease or condition is located in multiple regions, or if an agent is best delivered over a range of locations.

IX. EXAMPLES

Example 1. Preparation of System in Accordance with Goldberg et al, U.S. Pat. No. 10,398,655 "Goldberg"

Preparation of Microparticles

All the reagents and chemicals used are excipient or pharmaceutical grade.

Solution A: 0.1% (cisplatin) in 0.1% Tripolyphosphate (STPP) solution

Solution B: 0.1% Chitosan (CL 113) in 0.175% acetic acid solution 10 mL solution B was placed in a glass beaker and stirred at 600 rpm on magnetic stirrer. Transferred a total of 10 mL Solution A drop wise on the stirred solution B with the help of a peristaltic pump or any other pump that can provide a constant flow rate, as used herein at 1.5 mL/min, but which may be modified to yield a different size, charge, polydispersity, NP yield, and drug encapsulation efficiency properties.

Different ratios of solutions A to solution B (A:B) were used from 1:1 (as in the above case) to 1.1:0.85. Gradually increased the stirring speed of solution B to 650 rpm at the time when half of the solution A has been transferred. Following completion of the transfer of solution A, gradually increased the stirring speed to 700 rpm and then gradually added disaccharide trehalose to the solution to obtain a final trehalose concentration of 2%. Continued stirring until all the added trehalose was dissolved (or for at least 10 min) to equilibrate the solution. Measured the Z-average, the polydispersity index (PDI), the mean diameter of each peak, and microparticle yield (count rate) of the obtained microparticles.

For storage, the final microparticle solution is placed in a proper container and is frozen using liquid nitrogen, in dry ice, or in ultra-low temperature freezer until complete freezing obtained and then they are freeze-dried until complete elimination of solvent is obtained.

Preparation of Matrix

A device was made in accordance with the teachings of Goldberg using processes A though F as described herein.

A. An aqueous polymeric mixture was prepared of chitosan, with propylene glycol (in a concentration of 5% to 25% wt. percent) as a hydration promoter, HPMC (in a concentration of 0.1-10% wt. percent) as a particle adhesion inhibitor, and sucralose (in a concentration of 0.1 to 30% wt. percent) as a microparticle aggregation inhibitor.

B. To this mixture were added an active pharmaceutical ingredient, chitosan coated cisplatin microparticles having an average diameter between 500 nm and 2000 nm in a concentration of 10-40% percent by wt.

C. The resulting mixture was stirred for up to 3 hours at room temperature

D. The mixture was frozen and lyophilized under conditions of 0-5000 mTorr.

E. The resulting freeze-dried product is a matrix containing chitosan coated cisplatin microparticles embedded in a polymeric matrix.

F. The matrix was then applied to a water-permeable backing layer and cut to size, resulting in a device (called here a "patch") in accordance to the teachings of Goldberg.

Example 2. Preparation of Enhanced Device

Figure 2:
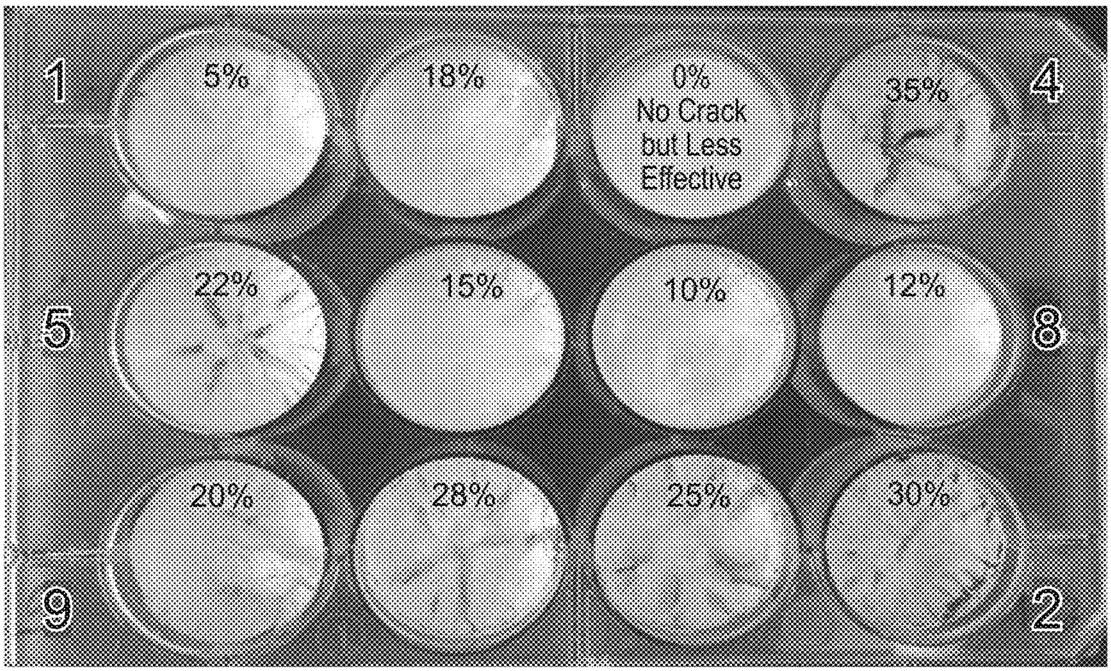
FIG. 2 is photograph of cisplatin-containing patches made with concentrations of sodium chloride in respective amounts (as marked) of 0%, 5%, 10%, 12%, 15%, 18%, 20%, 22%, 25%, 28%, and 30% and illustrating cracking resulting at elevated concentrations.

A device was made in a manner following the procedures of steps A though F of Example 1, but with the difference that, in step A, the aqueous mixture also contained sodium chloride in various concentrations as enumerated herein. The results are summarized in Table 1. Most concentrations caused significant issues with the patch's physical properties, clinical administration, and potency. FIG. 2 is photograph of cisplatin-containing patches made with concentrations of sodium chloride in respective amounts (as marked) of 0%, 5%, 10%, 12%, 15%, 18%, 20%, 22%, 25%, 28%, and 30% and illustrating cracking resulting at elevated concentrations. Even at concentrations wherein the cracks were no longer an issue, the concentrations of sodium chloride were still too high, because the patches were rigid and the rigidity and stiffness of the patches made them difficult to apply topically to irregularly shaped tumors. In addition, sodium chloride caused an overall lack of structural integrity of the particles embedded in the matrix and the release profile was an immediate burst, rather than a controlled release The following chart shows the effect of various concentrations of sodium chloride:

TABLE 1

Impact of varying salt concentrations on device performance

| Salt Concentration (% wt/wt) | Cell Uptake (In Vitro %) | Cell Death (2 hours) | In Vivo Efficacy (% Tumor reduction) | In Vitro Release (%) | Surface Charge (mV) | Notes |
|---|---|---|---|---|---|---|
| 0% | 96% | 25% | −40% | 49.6% | 52.1 | High charge and cell uptake but poor cell death |
| 5% | 91% | 28% | −52% | 51.3% | 43.3 | High charge and cell uptake but poor cell death |
| 10% | 90% | 36% | −86% | 76.9% | 37.9 | Improved cell death; improved in vivo efficacy despite reduction in surface charge |
| 18% | 95% | 40% | −91% | 98.9% | 29.5 | Optimal balance of the best cell uptake, in vivo efficacy and release despite the lower surface charge |
| 20% | 85% | 34% | −85% | N/A | 26.2 | Improved cell death and improved in vivo efficacy; however too brittle to be clinically viable |
| 25% | 85% | 28% | N/A | N/A | 22.9 | The high salt concentration caused the patch to be too brittle. It was not useable. |
| 35% | 83% | 24% | N/A* | N/A | 17.4 | The high salt concentration caused the patch to be too brittle. It was not useable. |

In this embodiment, the freeze-dried equivalent concentrations of 35% wt/wt and 18% wt/wt corresponds with the liquid concentration of 0.9% w/v and 0.12% w/v, respectively.

Figure 3:
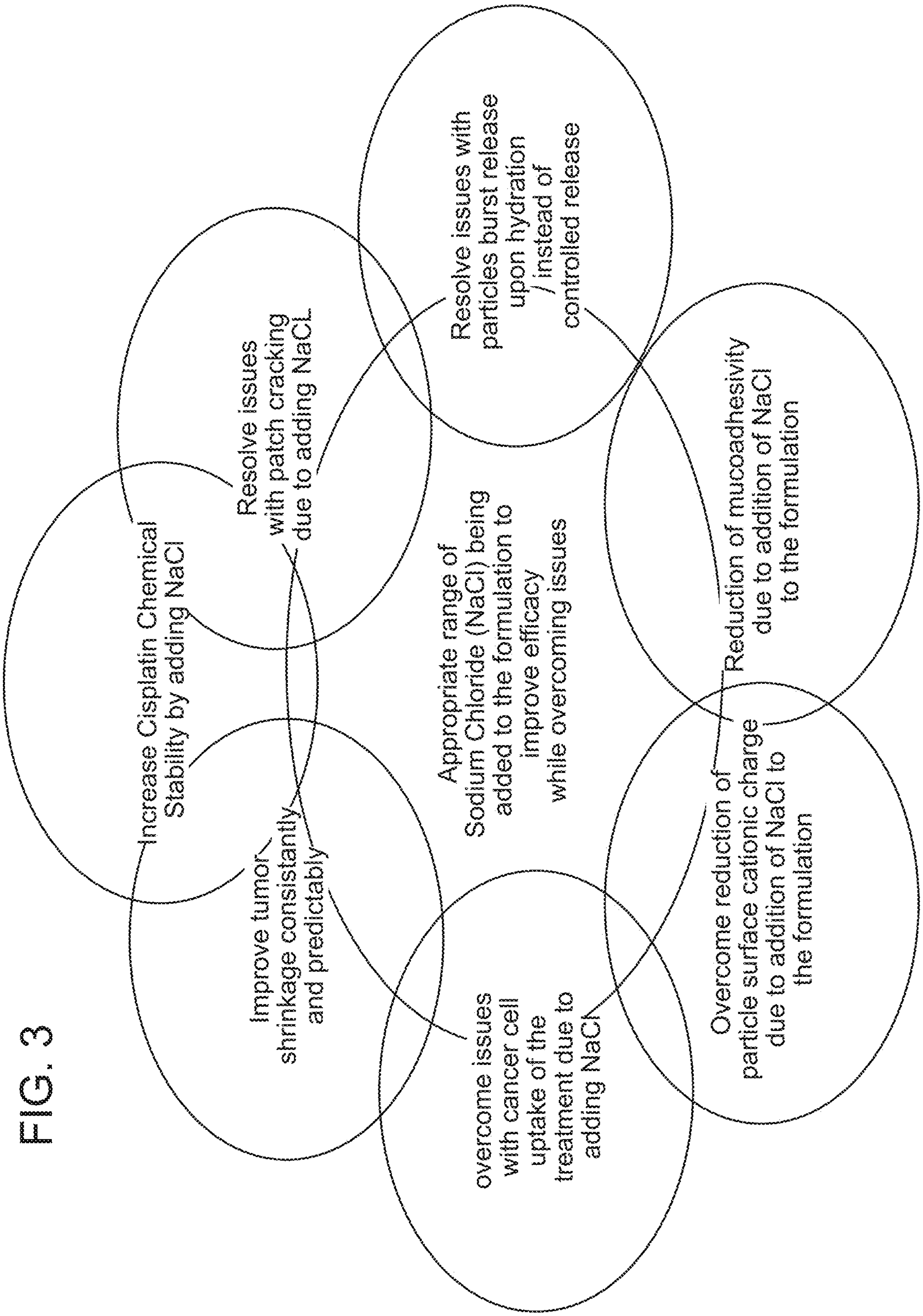
FIG. 3 is diagram illustrating changes in properties of cisplatin-containing patches, attributable to the presence of sodium chloride, that complicated optimization of the resulting patch. Adding NaCl to the formulation improved the chemical stability of cisplatin which is an active agent in one of the embodiments of the present invention. However, this change caused several issues and unexpected problems, such as causing physical breakage of the patch once dried, increased stiffness of the patch unsuitable for topical application, decrease of cationic surface charge of particles, reduced mucoadhesivity and cell uptake.

After the testing described herein, too much salt resulted in patches that were too brittle and were unusable, while too little salt showed suboptimal in vivo efficacy. FIG. 3 is a diagram illustrating changes in properties of cisplatin-containing patches, attributable to the presence of sodium chloride, that complicated optimization of the resulting patch. A preferred outcome produced a patch that remained physically pliable, while having improved cell death capabilities and superior in vivo tumor reduction.

Sodium chloride in a range between 10.0 wt/wt % and 18.0 wt/wt % in the freeze-dried patch maintained chemical stability of cisplatin, preventing premature hydrolysis of the drug prior to entering cells, and maintained the patch performance characteristics such as the release profile, the surface cationic charge and physical integrity. The concentration range between 10.0 wt/wt % and 18.0 wt/wt % sodium chloride in the freeze-dried patch made it possible to protect the active drug and to enhance the effect of cisplatin, all while utilizing amount of sodium chloride considerably lower than taught by the prior art. Nevertheless, to an person of ordinary skill in the art, it would not make sense to use the 0.12% w/v concentration rather than the 0.9 w/v %, as it is far less than the minimum necessary to prevent hydrolysis.

TABLE 2

| Context | Sodium Concentration Liquid | Equivalent Sodium Concentration After Freeze Drying |
|---|---|---|
| Known embodiment | 0.9% wt/v | 35% wt/wt |
| Present invention | 0.12% wt/v | 18% wt/wt |

Figure 4:
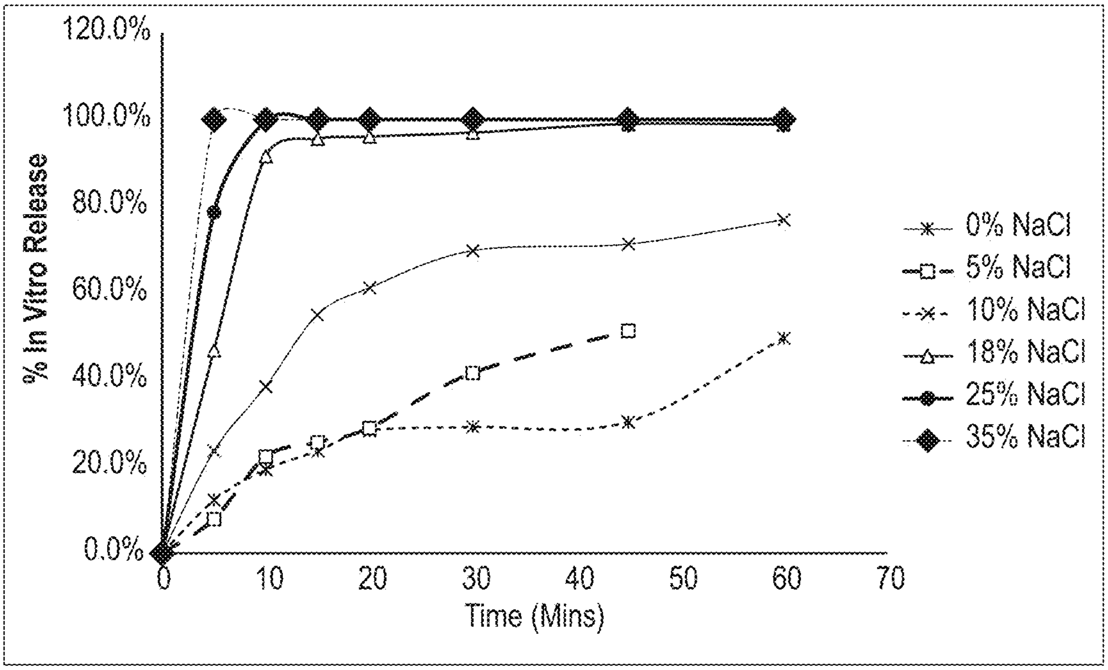
FIG. 4 is a set of graphs showing in vitro dissolution profiles of patches made in sodium concentrations varying from 0% to 35%.

Enhanced Release Profile. We found that in the optimum range of sodium concentration, the release of the particles from the patch matrix during patch administration was also enhanced, shown in human trials. FIG. 4 is a set of graphs showing in vitro dissolution profiles of patches made in sodium concentrations varying from 0% to 35%; it can be seen that the release profile at 18%, while slower than at 0%, is more linear and smoother. This improvement in release provided clinical benefit during the trials as the enhanced and consistent release of particles from the matrix of the patch, reduced patch-to-patch dose variability.

Figure 5:
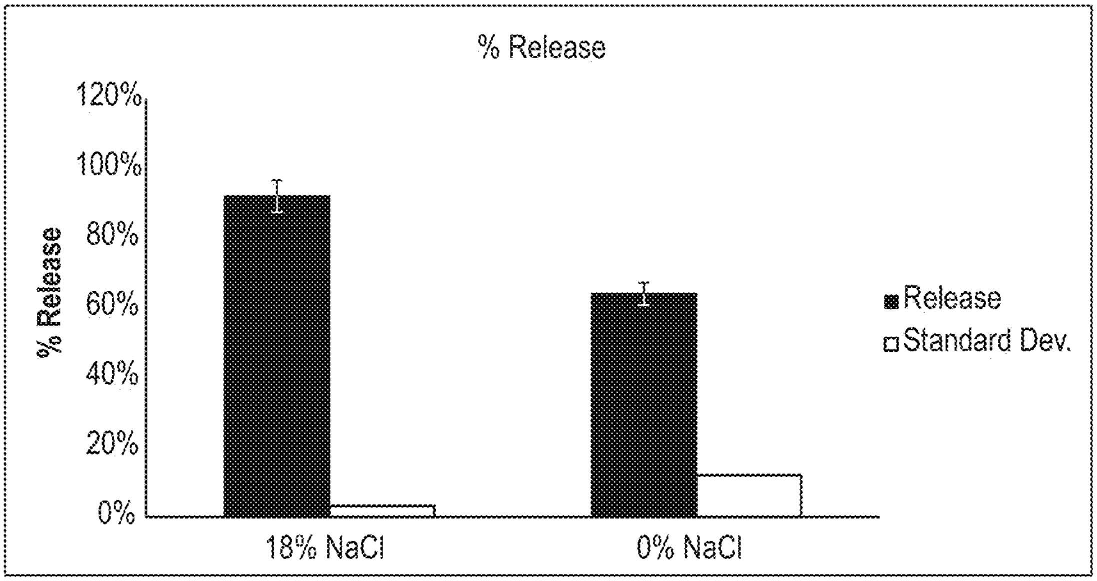
FIG. 5 is a set of bar graphs showing the percent release of drug from the patch when applied to tissue, based on concentration of sodium chloride in the patch, for 0% and 18%. The amount released was greater and more reproducible with the addition of NaCl than without (92%, 3.2% standard deviation vs. 65% and 12% standard deviation).

FIG. 5 is a set of bar graphs showing the percent release of drug from the patch when applied to tissue, based on concentration of sodium chloride in the patch, for 0% and 18% wt/wt. Patches containing the newly developed concentration of sodium chloride (at 18.0 wt/wt %) elicited superior dose precision and release (92% vs 65% no sodium chloride) with a standard deviation of only 3.2% (n=182 patches) compared with a standard deviation of 12% for patches lacking sodium chloride.

Figure 6:
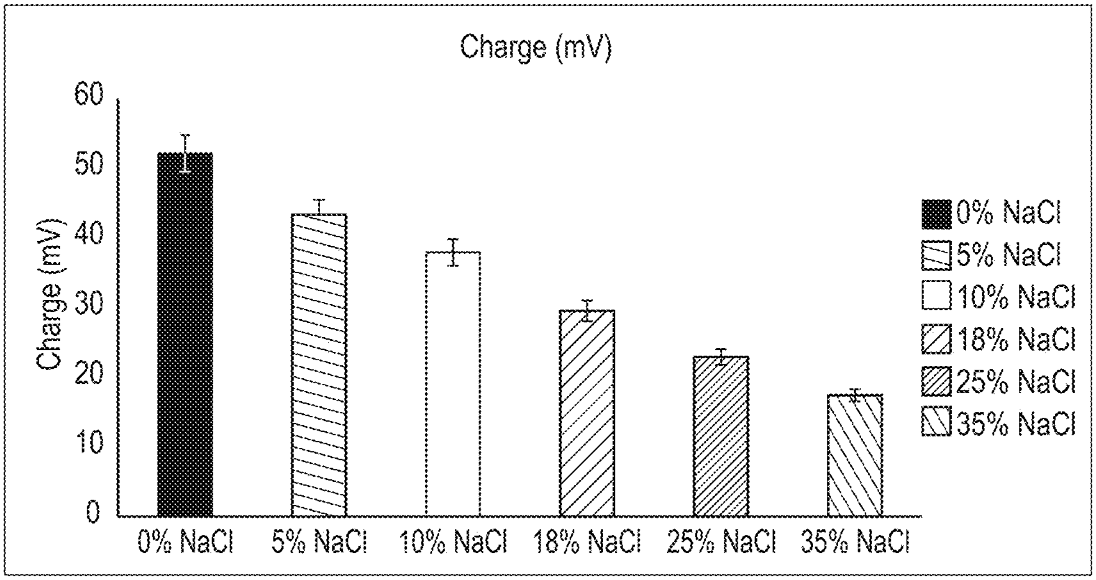
FIG. 6 is a set of bar graphs showing microparticle charge data obtained for various concentrations of NaCl in the patch ranging from 0% to 35%. There is a linear trend between the amount of NaCl present and decreasing charge.

Improved Performance: According to literature, higher concentrations of "charge screeners" such as sodium chloride decrease the surface charge (also known as zeta potential) of the particles (International Standard ISO 13099-1, 2012, "Colloidal systems—Methods for Zeta potential determination—Part 1: Electroacoustic and Electrokinetic phenomena")(Dukhin, A. S.; Goetz, P. J. (2017). Characterization of liquids, nano- and micro-particulates and porous bodies using Ultrasound. Elsevier)(Russel, W. B.; Saville, D. A.; Schowalter, W. R. (1989). Colloidal Dispersions. Cambridge University Press). This reduction of surface charge in theory should lead to decreased patch efficacy due to poor cell uptake and lower particle stability. FIG. 6 is a set of bar graphs showing microparticle charge data obtained for various concentrations of NaCl in the patch ranging from 0% to 35%. FIG. 6 shows that there is a linear trend between the amount of NaCl present and decreasing charge.

Figure 7:
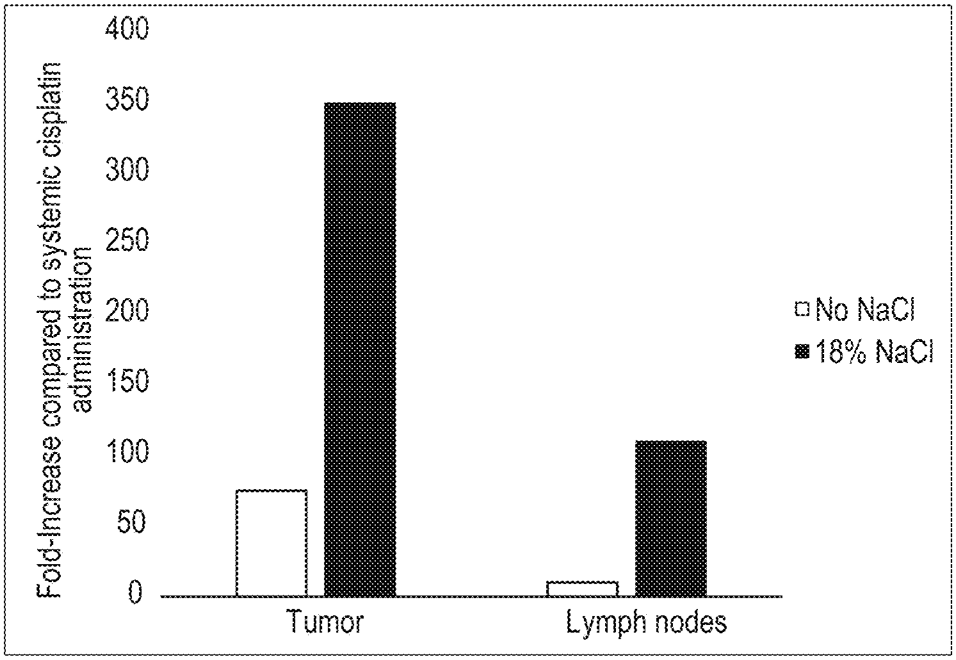
FIG. 7 presents two bar graphs showing biodistribution data comparing tumors and lymph nodes treated with patches containing 18% sodium chloride by weight and patches lacking sodium chloride.

FIG. 7 presents two bar graphs showing biodistribution data comparing tumors and lymph nodes treated with patches containing 18% sodium chloride by weight and patches lacking sodium chloride. This figure shows that, despite the reduction in surface charge caused by the increased sodium chloride concentration, the addition of sodium chloride, in the ranges described in this application, surprisingly improved the drug tissue retention in tumor and lymph nodes by over 400% and 1000%, respectively, as compared to the formulation of Example 1. This improvement has been shown in the clinical trial testing of the formulation in this application compared to that referenced in Example 1.

FIG. 8A is a photograph showing application of a patch, in accordance with an embodiment of the present invention, to the buccal mucosa, and FIG. 8B is a photograph showing application of a patch to a mucosal lesion on the anterior two-thirds of the tongue.

Figure 9:
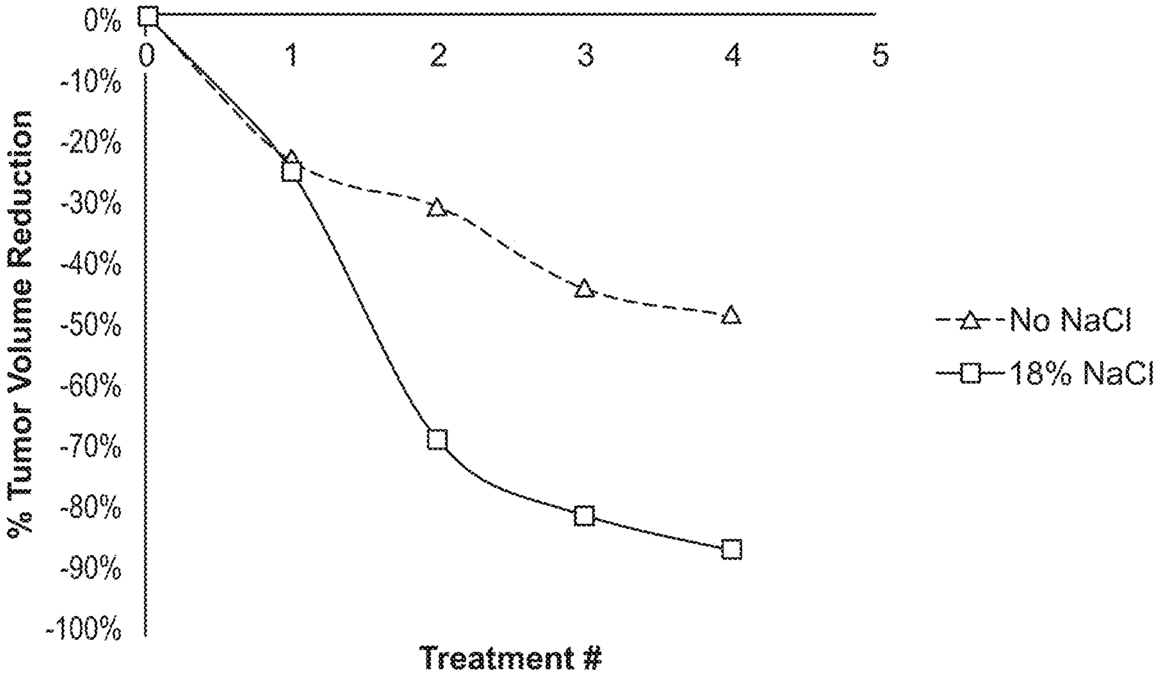
FIG. 9 presents two plots of percentage of tumor volume reduction as a function of time for use of a patch that includes 18% NaCl and for use of a patch that lacks NaCl. Patches with NaCl showed more rapid response and a higher rate of shrinkage than those without.

FIG. 9 presents two plots of percentage of tumor volume reduction as a function of time for use of a patch in accordance with an embodiment of the present invention that includes 18% NaCl and for use of a patch that lacks NaCl. This figure shows that the rate of tumor volume reduction is vastly improved in the current embodiment compared to the Example 1 formulation.

Example 3. Preparation of System 0.676 g chitosan was mixed in 3372 g of purified water under constant stirring at 500 RPM. 6.29 g of acetic acid was added to the mixture and the chitosan was further stirred at 500 RPM until dissolved. 1.01 g of Sodium chloride was dissolved in 844 g of purified water and heated to 37 degrees Celsius. To this, 1.26 g of cisplatin was added and dissolved for 30 minutes. 0.169 g of sodium tripolyphosphate was added and mixed for 5 minutes until dissolved at 500 RPM. The cisplatin-sodium tripolyphosphate solution was added at a constant flowrate to the chitosan solution, forming microparticles.

A sucralose solution was prepared by adding 1.26 g of sucralose to 12.6 g of purified water and vortexing for 1 minute. 0.633 g of chitosan was mixed in purified water under constant stirring at 500 RPM for 3 minutes. 3.36 g of acetic acid was added to the mixture and the chitosan was further stirred until dissolved. To this solution, 0.211 g of hypromellose and 422 microliters of propylene glycol were added and stirred until completely dissolved. This solution, along with the sucralose solution, were then combined with the microparticles and thoroughly mixed to create drug product solution.

The drug product solution was dispensed into molds and blast frozen. Molds were transferred to a lyophilizer and the drug product was freeze-dried until all moisture was removed.

TABLE 3

| System Components | | |
|---|---|---|
| Component | Weight (g) | Component Weight Percent (% w/w) |
| Microparticles | | |
| Chitosan | 0.676 | 11.95 |
| Sodium Chloride | 1.01 | 17.86 |
| Cisplatin | 1.26 | 22.28 |
| STPP | 0.169 | 2.99 |
| Microparticles Total | 3.115 | 55.07 |
| Polymer Matrix | | |
| Sucralose | 1.26 | 22.28 |
| Chitosan | 0.633 | 11.19 |
| Hypromellose | 0.211 | 3.73 |
| Propylene Glycol | 0.437 | 7.73 |
| Matrix Total | 2.541 | 44.93 |
| System | | |
| System Total | 5.656 | 100.00 |

TABLE 4

| Systems | | | |
|---|---|---|---|
| Chemotherapeutic | Chitosan [mg/mL] | TPP [mg/mL] | Formulation Volumetric Ratio Chitosan:Drug + TPP |
| Carboplatin | 1.0 | 0.45 | 1.1:0.85 |
| Cisplatin | 0.2 | 0.2 | 4.0:1.0 |
| Oxaliplatin | 1.0 | 0.45 | 1.1:0.85 |
| Malonato Platinum | 1.0 | 1.0 | 1.6:1.0 |
| Ormaplatin | 1.0 | 1.0 | 2.6:1.0 |
| 5-Fluorouracil | 0.2 | 0.2 | 3.25:1.0 |
| NAADP | 1.0 | 0.95 | 1.3:1.0 |
| Allantoin | 0.2 | 0.2 | 4.0:1.0 |
| Insulin | 1.0 | 0.85 | 1.1:0.85 |
| FITC | 0.2 | 0.2 | 4.0:1.0 |
| Rapamycin | 1.0 | 0.85 | 1.5:1.0 |

Example 4. Treatment of Lip Cancer

Figure 11:
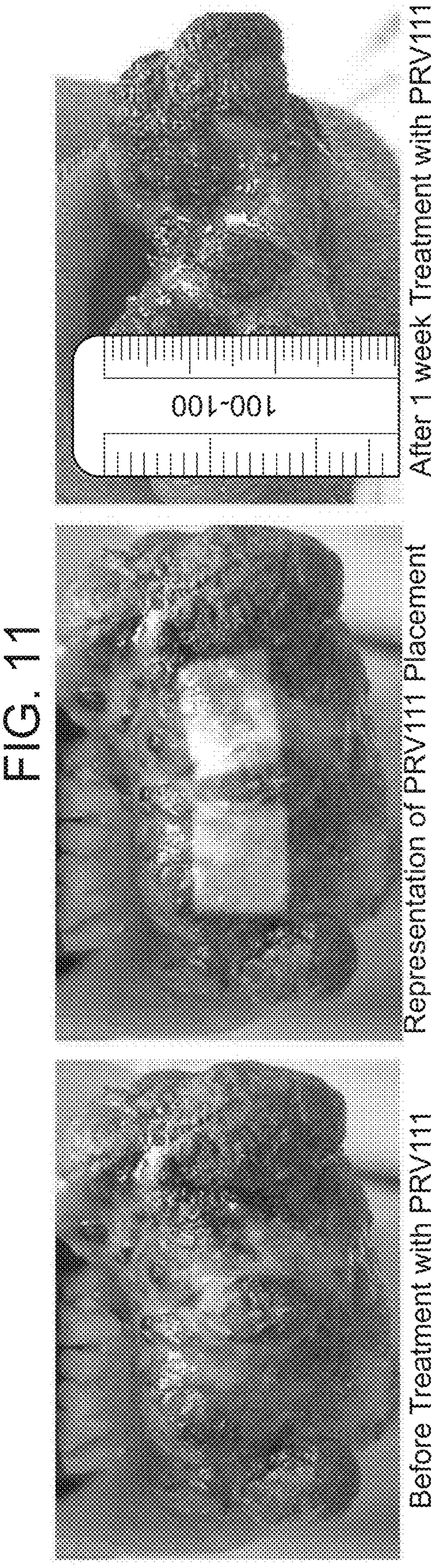
FIG. 11 shows treatment of a patient over the course of only one week. This was a T4 tumor patient. Per the protocol, two patches were used in an attempt to cover the tumor in each application however. The treatment reduced the tumor volume by over 50% as shown in the before and after photos.

A patient was diagnosed with advanced stage 4 lip SCC and had a poorly differentiated tumor identified as very fast growing tumor. The patient was treated with patches for 1 week which included 4 treatment visits, every other day. The dosing involved 12 mg of cisplatin in each visit (3 repeat application of 2 patches placed adjacent to one another for 10 mins). The patient received in total 48 mg of cisplatin in 1 week. Patient showed significance response to the treatment, including safety, and reduction in tumor size (FIG. 11).

Example 5. Treatment of Psoriasis

Figure 12:
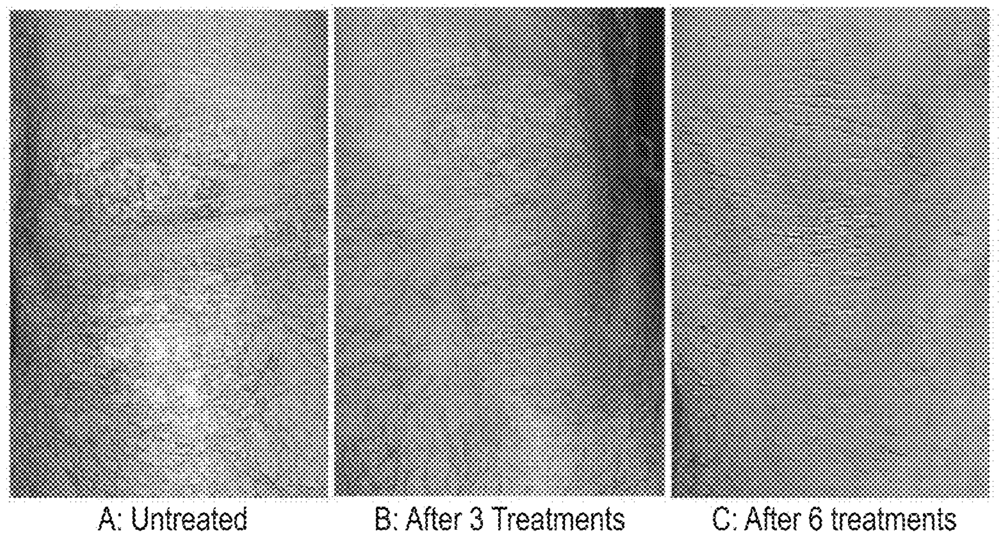
FIG. 12A-C shows human data using nanoengineered to treat moderate psoriasis with a suitable patch during treatment visits 3 times a week.
Figure 13:
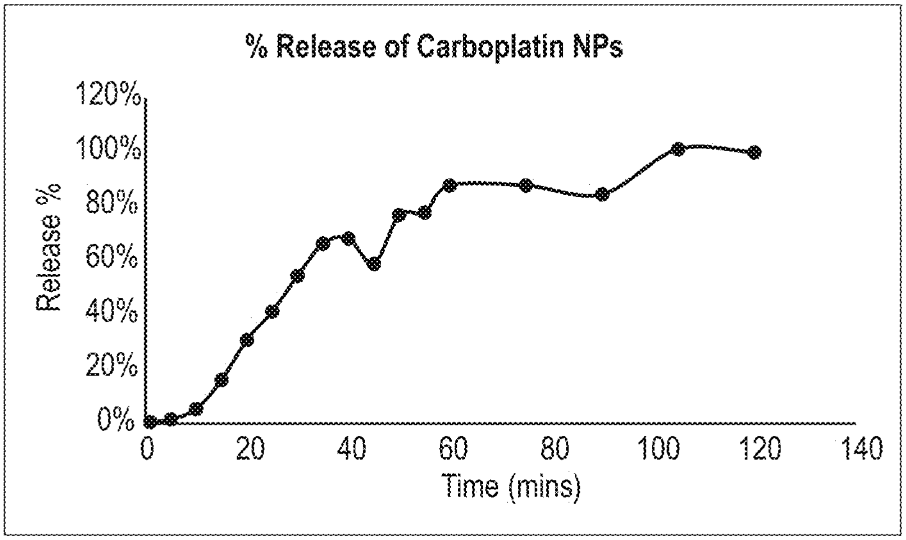
FIG. 13 shows percent release for carboplatin particles from a system of the present invention.

A patch was manufactured the same way as described above, using allantoin instead of cisplatin. The patient suffering from moderate psoriasis was treated three times a week using the allantoin patch. See FIG. 12.

The embodiments of the present invention described above are intended to be merely exemplary; numerous variations and modifications will be apparent to those skilled in the art. All such variations and modifications are intended to be within the scope of the present invention as defined in any appended claims. Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A system comprising:

a polymeric matrix comprising:

chitosan having a concentration of from about 20 to about 30% (w/w) of the polymeric matrix;

a chloride salt of a monovalent cation having a concentration of from about 10 to about 18% (w/w) of the polymeric matrix;

a hydration promoter having a concentration of from about 5 to about 25% (w/w) of the polymeric matrix:

a particle adhesion inhibitor having a concentration of from about 0.1 to about 10% (w/w) of the polymeric matrix;

a particle aggregation inhibitor in having a concentration of from about 0.1 to about 30% (w/w) of the polymeric matrix; and a plurality of microparticles each comprising a chitosan coating and a therapeutic agent;

wherein the microparticles have an average diameter between 500 nm and 2000 nm and are present in an amount of from about 10 to about 40% (w/w) of the polymeric matrix.

2. The system of claim 1, wherein the chitosan has a molecular weight of from about 80 kDa to 200 kDa.

3. The system of claim 1, wherein the chloride salt of a monovalent cation is NaCl, KCl, LiCl, RbCl, CsCl, $NH_4Cl$, or combinations thereof.

4. The system of claim 1, wherein the chloride salt of a monovalent cation is NaCl.

5. The system of claim 1, wherein the chloride salt of a monovalent cation is NaCl and is present in the polymeric matrix in an amount of about 18% (w/w) of the polymeric matrix.

6. The system of claim 1, wherein the therapeutic agent comprises an antineoplastic agent.

7. The system of claim 1, wherein the therapeutic agent comprises cisplatin.

8. The system of claim 1, wherein the hydration promoter is ethylene glycol, propylene glycol, beta-propylene glycol, glycerol, or combinations thereof.

9. The system of claim 8, wherein the hydration promoter is propylene glycol .

10. The system of claim 9, wherein the propylene glycol is present in an amount of about 7.75% (w/w) of the polymeric matrix.

11. The system of claim 1, wherein the particle adhesion inhibitor comprises hydroxypropylmethylcellulose (HPMC).

12. The system of claim 11, wherein the hydroxypropylmethylcellulose (HPMC) is present in an amount of about 3.7% (w/w) of the polymeric matrix.

13. The system of claim 1, wherein the particle aggregation inhibitor is a monosaccharide, disaccharide, sugar alcohol, chlorinated monosaccharide, chlorinated disaccharide, or combinations thereof.

14. The system of claim 1, wherein the particle aggregation inhibitor is sucralose.

15. The system of claim 14, wherein the sucralose is present in an amount of about 22.25% (w/w) of the polymeric matrix.

16. The system of claim 1, wherein the polymeric matrix further comprises a free amount of the therapeutic agent in an amount of from about 20 to about 80% of the total amount of the therapeutic agent in the system.

17. The system of claim 1, wherein the therapeutic agent is cisplatin and is present in an amount of from about 1 to about 50% (w/w) of the polymeric matrix.

18. The system of claim 1, wherein the therapeutic agent is cisplatin and is present in an amount of about 22.5% (w/w) of the polymeric matrix.

19. The system of claim 1, wherein the microparticles further comprise sodium tripolyphosphate.

20. The system of claim 19, wherein the sodium tripolyphosphate is present in an amount of from about 0.1 to about 10% (w/w) of the polymeric matrix.

21. The system of claim 19, wherein the sodium tripolyphosphate is present in an amount of about 3.0% (w/w) of the polymeric matrix.

22. The system of claim 1, wherein the polymeric matrix comprises:

chitosan in an amount of from about 20 to about 30% (w/w);

cisplatin in an amount of from about 20 to about 30% (w/w);

NaCl in an amount of from about 10 to about 18% (w/w);

propylene glycol in an amount of from about 5 to about 25% (w/w);

hydroxypropylmethylcellulose (HPMC) in an amount of from about 0.1 to about 10% (w/w);

sucralose in an amount of from about 0.1 to about 30% (w/w); and the microparticles in an amount of from about 10 to about 40% (w/w).

23. The system of claim 1, wherein the polymeric matrix comprises:

chitosan in an amount of about 22.5% (w/w);

cisplatin in an amount of about 22.5% (w/w);

NaCl in an amount of about 18% (w/w) of the polymeric matrix;

propylene glycol in an amount of about 7.75% (w/w);

hydroxypropylmethylcellulose (HPMC) in an amount of about 3.7% (w/w); and sucralose in an amount of about 22.25% (w/w).

24. A method of administering a therapeutic agent to a subject in need thereof, comprising applying a system of claim 1 to the subject such that at least 50% of a therapeutic agent of the system is released from the system in less than 30 minutes.

25. A method of preparing a system of claim 1, comprising:

forming a first mixture comprising water, chitosan, a chloride salt of a monovalent cation, a hydration promoter, a particle adhesion inhibitor, and a particle aggregation inhibitor, to prepare a matrix mixture;

forming a second mixture comprising the matrix mixture and microparticles comprising a chitosan coating and a therapeutic agent, wherein the microparticles have an average diameter between 500 nm and 2000 nm;

removing the water from the second mixture, to prepare a dried mixture; and applying the dried mixture to a backing layer, thereby preparing the system.

26. A method of preparing a system of claim 19, comprising forming a first mixture comprising water, chitosan, and acetic acid;

forming a second mixture comprising a chloride salt, a therapeutic agent, and sodium tripolyphosphate;

forming a third mixture comprising the first mixture and the second mixture, thereby forming microparticles comprising a chitosan coating and a therapeutic agent, wherein the microparticles have an average diameter between 500 nm and 2000 nm;

forming a fourth mixture comprising water, chitosan, acetic acid, a hydration promoter, and a particle adhesion inhibitor;

forming a fifth mixture comprising the fourth mixture, a particle aggregation inhibitor, and the microparticles, to form the polymer matrix;

removing the water from the polymer matrix, to prepare a dried mixture; and applying the dried mixture to a backing layer, thereby preparing the system.

27. A method of treating a skin disease of a subject in need thereof, comprising applying a system of claim 1 to the skin of the subject such that a therapeutically effective amount of a therapeutic agent of the system is released from the system and administered to the skin of the subject, thereby treating the skin disease.

28. A method of treating a mucosal cancer, comprising applying the system of claim 1 to the mucosal cancer of a subject in need thereof, thereby treating the mucosal cancer.

* * * * *